US008242258B2

(12) United States Patent
Dellinger et al.

(10) Patent No.: US 8,242,258 B2
(45) Date of Patent: *Aug. 14, 2012

(54) PROTECTING GROUPS FOR RNA SYNTHESIS

(75) Inventors: Douglas J. Dellinger, Boulder, CO (US); Brian Stell, Durham, NC (US); Marvin H. Caruthers, Boulder, CO (US)

(73) Assignees: Agilent Technologies, Inc., Santa Clara, CA (US); The Regents of the University of Colorado, Denver, CO (US)

( * ) Notice: Subject to any disclaimer, the term of this patent is extended or adjusted under 35 U.S.C. 154(b) by 490 days.

This patent is subject to a terminal disclaimer.

(21) Appl. No.: 11/949,667

(22) Filed: Dec. 3, 2007

(65) Prior Publication Data

US 2008/0194502 A1    Aug. 14, 2008

Related U.S. Application Data

(60) Provisional application No. 60/868,352, filed on Dec. 3, 2006.

(51) Int. Cl.
C07H 19/067    (2006.01)

(52) U.S. Cl. .............. 536/26.7; 536/26.8; 536/27.22; 536/27.23; 536/27.13; 536/28.4; 536/28.5; 536/28.53

(58) Field of Classification Search .............. None
See application file for complete search history.

(56) References Cited

U.S. PATENT DOCUMENTS

| | | | |
|---|---|---|---|
| 5,889,136 A | 3/1999 | Scaringe et al. | |
| 6,111,086 A | 8/2000 | Scaringe | |
| 6,222,030 B1 | 4/2001 | Dellinger et al. | |
| 6,590,093 B1 | 7/2003 | Scaringe | |
| 6,630,581 B2 | 10/2003 | Dellinger et al. | |
| 7,101,986 B2 | 9/2006 | Dellinger et al. | |
| 7,135,565 B2 * | 11/2006 | Dellinger et al. | 536/22.1 |
| 7,193,077 B2 * | 3/2007 | Dellinger et al. | 536/25.3 |
| 7,271,258 B2 * | 9/2007 | Dollinger et al. | 536/26.7 |
| 7,368,550 B2 * | 5/2008 | Dellinger et al. | 536/23.1 |
| 7,385,050 B2 * | 6/2008 | Dellinger et al. | 536/26.7 |
| 7,411,061 B2 * | 8/2008 | Myerson et al. | 536/23.1 |
| 7,417,139 B2 * | 8/2008 | Dellinger et al. | 536/25.3 |
| 7,427,679 B2 * | 9/2008 | Dellinger et al. | 536/26.7 |
| 7,435,810 B2 * | 10/2008 | Myerson et al. | 536/25.34 |
| 2002/0058802 A1 | 5/2002 | Dellinger et al. | |
| 2004/0116687 A1 | 6/2004 | Dellinger | |
| 2004/0127441 A1 * | 7/2004 | Gleave et al. | 514/44 |
| 2004/0266707 A1 * | 12/2004 | Leake et al. | 514/44 |
| 2005/0048496 A1 | 3/2005 | Dellinger et al. | |
| 2005/0048497 A1 | 3/2005 | Dellinger et al. | |
| 2005/0048601 A1 | 3/2005 | Dellinger et al. | |
| 2005/0049407 A1 | 3/2005 | Dellinger et al. | |
| 2005/0049411 A1 | 3/2005 | Dellinger et al. | |
| 2006/0247430 A1 | 11/2006 | Dellinger et al. | |
| 2006/0293511 A1 | 12/2006 | Dellinger | |
| 2007/0099859 A1 | 5/2007 | Dellinger et al. | |
| 2007/0100136 A1 | 5/2007 | Dellinger et al. | |
| 2007/0100137 A1 | 5/2007 | Dellinger et al. | |
| 2007/0100138 A1 | 5/2007 | Dellinger et al. | |
| 2008/0076913 A1 * | 3/2008 | Dellinger et al. | 536/25.31 |
| 2008/0146787 A1 * | 6/2008 | Timar et al. | 536/23.1 |
| 2008/0194502 A1 * | 8/2008 | Dellinger et al. | 514/43 |

OTHER PUBLICATIONS

Sekine et al., "Cyclic Orthoester Functions a New Protecting Groups in Nucleosides," J. American Chemical Society, 105(7), 2044-2049 (1983).*
Scaringe, S., "RNA Oligonucleotide Synthesis via 5'-Silyl-2'-Orthoester Chemistry," Methods, 23(3), 206-2178 (Mar. 2001).*
Karwowski et al., "4,5-Bis(Ethoxycarbonyl)-[1,3]Dioxolan-2-yl as a New Orthoester-Type Protecting Group for the 2'-Hydroxyl Function in the Chemical Synthesis of RNA" Nucleosides, nucleotides, and nucleic acids (2005) vol. 24 No. 5-7, pp. 1111-1114.*
Sekine et al., "Synthesis of 2'-O-(1,3-Benzodithiol-2-yl)uridine and Related Compounds as Key Intermediates in Oligoribonucleotide Synthesis" J. Org. Chem. (1983) vol. 48 pp. 3112-3114.*
Ogilvie et al., "Conversion of uridine 2',3'-carbonates to anhydrouridines" Canadian Journal of Chemistry (1969) vol. 47 pp. 495-497).*
Scaringe et al., "Novel RNA Synthesis Method Using 5_-O-Silyl-2_-O-orthoester Protecting Groups" J. Am. Chem. Soc. (1998) vol. 120 pp. 11820-11821.*

* cited by examiner

Primary Examiner — Eric S Olson

(57) ABSTRACT

Aspects of the invention include 2' protected nucleoside monomers that are protected at the 2' site with orthoester-type protecting groups. The 2' protected monomers also include a second, aryl carbonate-type, protecting group. Aspects of the invention further include nucleic acids that include the protecting groups of the invention, as well as methods of synthesizing nucleic acids using the protecting groups of the invention.

20 Claims, 1 Drawing Sheet

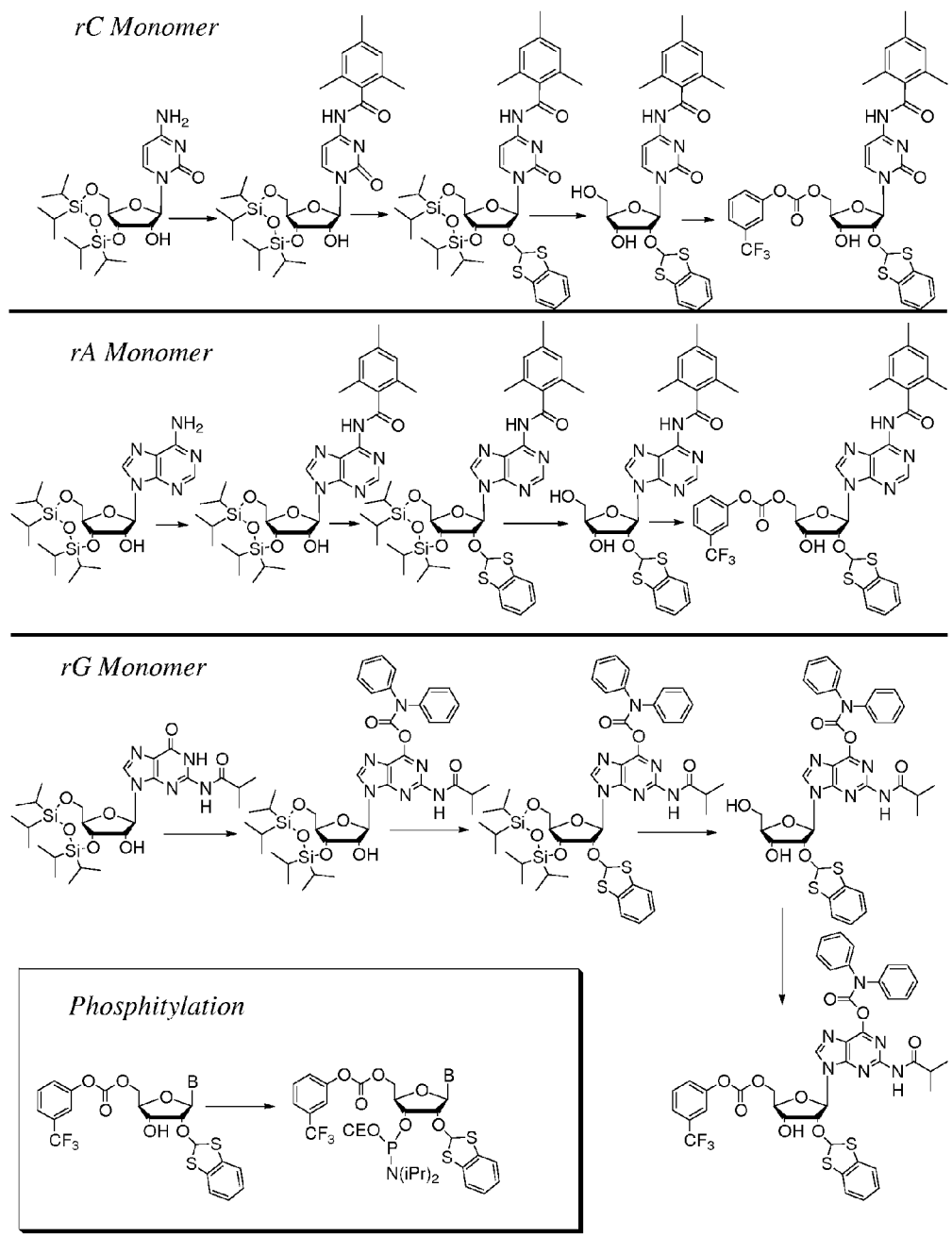

US 8,242,258 B2

PROTECTING GROUPS FOR RNA SYNTHESIS

CROSS REFERENCE TO RELATED APPLICATION

This application claims the benefit under 35 U.S.C. §119(e) of prior U.S. provisional application Ser. No. 60/868,352 filed Dec. 3, 2006, now expired, the disclosure of application is herein incorporated by reference.

INTRODUCTION

Chemical synthesis of RNA is a much more difficult task than chemical synthesis of DNA, because the 2'-hydroxyl group in the ribose has to be protected during chemical synthesis. The close proximity of a protected 2'-hydroxyl to the internucleotide phosphate presents problems, both in terms of formation of the internucleotide linkage and in the removal of the 2'-protecting group once the oligoribonucleotide is synthesized. In addition, the internucleotide bond in RNA is far less stable than that in DNA.

Until recently, the typical approach to RNA synthesis (see FIG. 1) utilized ribonucleoside monomers in which the 5'-hydroxyl group was protected by the acid-labile dimethoxytrityl (DMT) protecting group, which can be removed under acidic conditions after coupling of the monomer to the growing oligoribonucleotide. Various acid-stable protecting groups have been placed on the 2'-hydroxyl to prevent isomerization and cleavage of the internucleotide bond during the acid deprotection step. The most popular of these acid-stable protecting groups seems to be the tert-butyl-dimethylsilyl group, known as TBDMS (Ogilvie et al., 1979). The use of TBDMS as 2'-protecting group dominated the previously small market for RNA chemical synthesis for a very long time (Usman et al., 1987; Ogilvie et al., 1988).

However, oligoribonucleotide syntheses carried out using TBDMS are by no means satisfactory and typically produce RNA products of poor quality. As a result, the TBDMS protecting group migrates from the 2'-position to the 3'-position. Furthermore, during the synthesis of the monomer (e.g., 5'-O-DMT-2'-O-TBDMS-ribo-3'-O-(beta-cyanoethyl, N-diisopropyl)phosphoramidite), introduction of the 2'-silyl group is non-regioselective, thus it can be added to either the 2' or 3' position. Combined with the added chemical requirements to prevent migration of the silyl group during phosphoramidite production, synthesis of the monomer is challenging and costly. It is also well known in the art that the coupling efficiency of these monomers is greatly decreased due to steric hindrance of the 2'-TBDMS protecting group, which not only affects the yield and purity of the full-length product, but also limits the length of the oligoribonucleotide that can be achieved by this method.

The demand for synthetic RNA has been increasing, largely due to the discovery of RNA interference. Therefore, it is desirable to develop improved RNA synthesis schemes, particularly 2'-protecting groups, to meet the growing needs.

SUMMARY

Aspects of the invention include 2' protected nucleoside monomers that are protected at the 2' site with orthoester-type protecting groups. The 2' protected monomers also include a second, aryl carbonate-type, protecting group. Embodiments of the orthoester-type protecting groups include orthoester protecting groups as well as orthothioester protecting groups. Embodiments of the acyl carbonate-type protecting groups include acyl carbonate protecting groups as well as acyl thiocarbonate protecting groups. Aspects of the invention further include nucleic acids that include the protecting groups of the invention, as well as methods of synthesizing nucleic acids using the protecting groups of the invention.

BRIEF DESCRIPTION OF THE FIGURES

FIG. 1 illustrates a synthetic strategy for producing nucleotide compositions, wherein regioselective introduction of a BDT group on the 2'-hydroxyl is performed after the transient protection of the 5' and 3'-hydroxyl groups using the Markewicz disilyloxane TIPS protecting group. The synthetic strategy includes the following steps for each of the rA, rC and rG monomers: 1) protection of the nucleobases of the 3',5'-TIPS derivatives, using standard methods; 2) protection of the 2'-hydroxyls with the BDT orthoester protecting group using standard methods; 3) removal of the Markewicz disilyloxane TIPS protecting group by reaction with fluoride, using standard methods; 4) protection of the 5'-hydroxyls to produce the 5'-(3-(trifluoromethyl)phenyl carbonates), using standard methods; 5) phosphitylation of the 3'-hydroxyls (shown in box) to give the protected ribonucleoside phosphoramidites of rA, rC and rG, using standard methods. Standard methods for each step are described in the art of polynucleotide synthesis and in Greene et al., "Protective Groups in Organic Synthesis," John Wiley and Sons, Third Edition, 1991.

DEFINITIONS

Prior to describing the invention in further detail, the terms used in this application are defined as follows unless otherwise indicated.

A "nucleotide" or "nucleotide moiety" refers to a sub-unit of a nucleic acid (whether DNA or RNA or analogue thereof) which includes a phosphate group, a sugar group and a heterocyclic base, as well as analogs of such sub-units. Other groups (e.g., protecting groups) can be attached to any component(s) of a nucleotide.

A "nucleoside" or "nucleoside moiety" references a nucleic acid subunit including a sugar group and a heterocyclic base, as well as analogs of such sub-units. Other groups (e.g., protecting groups) can be attached to any component(s) of a nucleoside.

A "nucleoside residue" refers to a molecule having a sugar group and a nitrogen containing base (as in a nucleoside) as a portion of a larger molecule, such as in a polynucleotide, oligonucleotide, or nucleoside phosphoramidite.

A "nucleotide monomer" refers to a molecule which is not incorporated in a larger oligo- or poly-nucleotide chain and which corresponds to a single nucleotide sub-unit; nucleotide monomers may also have activating or protecting groups, if such groups are necessary for the intended use of the nucleotide monomer.

The terms "nucleoside" and "nucleotide" are intended to include those moieties that contain not only the known purine and pyrimidine bases, e.g. adenine (A), thymine (T), cytosine (C), guanine (G), or uracil (U), but also other heterocyclic bases that have been modified. Such modifications include methylated purines or pyrimidines, acylated purines or pyrimidines, alkylated riboses or other heterocycles. Such modifications include, e.g., diaminopurine and its derivatives, inosine and its derivatives, alkylated purines or pyrimidines, acylated purines or pyrimidines thiolated purines or pyrimidines, and the like, or the addition of a protecting group such as acetyl, difluoroacetyl, trifluoroacetyl, isobutyryl, benzoyl, 9-fluorenylmethoxycarbonyl, phenoxyacetyl, dimethylformamidine, N,N-diphenyl carbamate, or the like. The purine or pyrimidine base may also be an analog of the foregoing; suitable analogs will be known to those skilled in the art and are described in the pertinent texts and literature. Common analogs include, but are not limited to, 1-methyladenine, 2-methyladenine, N6-methyladenine, N6-isopentyladenine, 2-methylthio-N6-isopentyladenine, N,N-dimethyladenine, 8-bromoadenine, 2-thiocytosine, 3-methylcytosine, 5-methylcytosine, 5-ethylcytosine, 4-acetylcytosine, 1-methylguanine, 2-methylguanine, 7-methylguanine, 2,2-dimethylguanine, 8-bromoguanine, 8-chloroguanine, 8-aminoguanine, 8-methylguanine, 8-thioguanine, 5-fluorouracil, 5-bromouracil, 5-chlorouracil, 5-iodouracil, 5-ethyluracil, 5-propyluracil, 5-methoxyuracil, 5-hydroxymethyluracil, 5-(carboxyhydroxymethyl)uracil, 5-(methylaminomethyl)uracil, 5-(carboxymethylaminomethyl)-uracil, 2-thiouracil, 5-methyl-2-thiouracil, 5-(2-bromovinyl)uracil, uracil-5-oxyacetic acid, uracil-5-oxyacetic acid methyl ester, pseudouracil, 1-methylpseudouracil, queosine, inosine, 1-methylinosine, hypoxanthine, xanthine, 2-aminopurine, 6-hydroxyaminopurine, 6-thiopurine and 2,6-diaminopurine.

In addition, the terms "nucleoside" and "nucleotide" include those moieties that contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like. "Analogues" refer to molecules having structural features that are recognized in the literature as being mimetics, derivatives, having analogous structures, or other like terms, and include, for example, polynucleotides incorporating non-natural (not usually occurring in nature) nucleotides, unnatural nucleotide mimetics such as 2'-modified nucleosides, peptide nucleic acids, oligomeric nucleoside phosphonates, and any polynucleotide that has added substituent groups, such as protecting groups or linking groups.

An "internucleotide bond" or "nucleotide bond" refers to a chemical linkage between two nucleoside moieties, such as the phosphodiester linkage in nucleic acids found in nature, or linkages well known from the art of synthesis of nucleic acids and nucleic acid analogues. An internucleotide bond may include a phospho or phosphite group, and may include linkages where one or more oxygen atoms of the phospho or phosphite group are either modified with a substituent or replaced with another atom, e.g., a sulfur atom, or the nitrogen atom of a mono- or di-alkyl amino group.

A "group" is substituted or unsubstituted. Substituents are selected from one or more lower alkyl, amino, imino, amido, alkylamino, arylamino, alkoxy, aryloxy, thio, alkylthio, arylthio, or aryl; or one or more hydrocarbyl, alkyl, aryl, aralkyl, alkoxy, thioalkyl, hydroxyl, amino, amido, amidine, sulfonyl, thio, mercapto, thioester, thioacetate, thioformate, imino, halo, hetereocyclic group, hydrocarbyl, cyano, nitro, nitrate, nitroso, azido, carboxy, acyl, alkoxycarbonyl, formyl, carbonate, sulfide, sulfone, sulfoxy, phosphoryl, phosphonate, phosphinate, sulfonate, sulfate, sulfamoyl, sulfonamide, silyl, silyloxy, or boronyl; optionally substituted on one or more available carbon atoms with a nonhydrocarbyl substituent that is cyano, nitro, halogen, hydroxyl, sulfonic acid, sulfate, phosphonic acid, phosphate, or phosphonate. It will be understood by those skilled in the art that the substitutents may themselves be substituted, if appropriate. Any substituents are chosen so as not to substantially adversely affect reaction yield (for example, not lower it by more than 20% (or 10%, or 5%, or 1%) of the yield otherwise obtained without a particular substituent or substituent combination). Further, substituents are chosen so as to be chemically compatible with the other groups present and to avoid side reactions known to those skilled in the art. For example, an alcohol would not be substituted with a lithium group, as the hydroxide of the alcohol and the lithium group are incompatible and would react with each other. For any group in this disclosure, each substituent may include up to 40, 35, 30, 25, 20, 18, 16, 14, 12, 11, 10, 9, 8, 7, 6, 5, 4 or 3 carbon atoms. Overall, the total number of carbon atoms in all the substituents for any group is, in certain embodiments, 80, 75, 70, 65, 60, 55, 50, 45, 40, 35, 30, 25, 20, 18, 16, 14, 12, 11, 10, 9, 8, 7, 6, 5, 4 or 3 or less.

The term "heterocycle", "heterocyclic", "heterocyclic group" or "heterocyclo" refers to fully saturated or partially or completely unsaturated cyclic groups having at least one heteroatom in at least one carbon atom-containing ring, including aromatic ("heteroaryl") or nonaromatic (for example, 3 to 13 member monocyclic, 7 to 17 member bicyclic, or 10 to 20 member tricyclic ring systems). Each ring of the heterocyclic group containing a heteroatom may have 1, 2, 3, or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system. The rings of multi-ring heterocycles may be fused, bridged and/or joined through one or more spiro unions. Nitrogen-containing bases are examples of heterocycles. Other examples include piperidinyl, morpholinyl and pyrrolidinyl.

The terms "substituted heterocycle", "substituted heterocyclic", "substituted heterocyclic group" and "substituted heterocyclo" refer to heterocycle, heterocyclic, and heterocyclo groups substituted with one or more groups preferably selected from alkyl, substituted alkyl, alkenyl, oxo, aryl, substituted aryl, heterocyclo, substituted heterocyclo, carbocyclo (optionally substituted), halo, hydroxy, alkoxy (optionally substituted), aryloxy (optionally substituted), alkanoyl (optionally substituted), aroyl (optionally substituted), alkylester (optionally substituted), arylester (optionally substituted), cyano, nitro, amido, amino, substituted amino, lactam, urea, urethane, sulfonyl, and the like, where optionally one or more pair of substituents together with the atoms to which they are bonded form a 3 to 7 member ring.

When used herein, the terms "hemiacetal", "thiohemiacetal", "acetal", and "thioacetal" refer to a chemical moiety in which a single carbon atom is seminally disubstituted with either two oxygen atoms or a combination of an oxygen atom and a sulfur atom. In addition, when using these terms, it is understood that the carbon atom may actually be seminally disubstituted by two carbon atoms, forming ketal, rather than acetal, compounds. The terms "orthoester" and "orthothioester" reference a moiety in which a single carbon atom is seminally trisubstituted with either three oxygen atoms or a combination of oxygen atom(s) and sulfur atom(s), e.g. compounds having the structure:

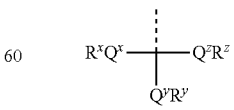

wherein $Q^x$, $Q^y$, and $Q^z$ independently oxygen or sulfur, and none of $R^x$, $R^y$, or $R^z$ is H. The term "orthoester-type" refers to both orthoesters and orthothioesters, i.e., compounds with the above structure.

The terms "carbonate" and "thiocarbonate" refer to a moiety wherein a single carbonyl carbon is substituted with either two oxygens, or with one oxygen and one sulfur, respectively, e.g., compounds having the structure:

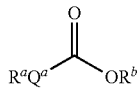

wherein $Q^a$ is either an oxygen or a sulfur and neither $R^a$ nor $R^b$ is H. The term "carbonate-type" refers to both carbonates and thiocarbonates.

The term "electron-withdrawing group" refers to a moiety that has a tendency to attract valence electrons from neighboring atoms (i.e., the substituent is electronegative with respect to neighboring atoms). A quantification of the level of electron-withdrawing capability is given by the Hammett sigma constant. This well known constant is described in many references, for instance, March, Advanced Organic Chemistry 251-59, McGraw Hill Book Company, New York, (1977). Electron-withdrawing groups include nitro, acyl, formyl, sulfonyl, trifluoromethyl, cyano, chloride, and the like.

The term "electron-donating group" refers to a moiety that has a tendency to repel valence electrons from neighboring atoms (i.e., the substituent is less electronegative with respect to neighboring atoms). Electron-donating groups include amino, methoxy, alkyl (including C1-6 alkyl that can have a linear or branched structure), C4-9 cycloalkyl, and the like.

The phrase "protecting group" as used herein refers to a species which prevents a portion of a molecule from undergoing a specific chemical reaction, but which is removable from the molecule following completion of that reaction. A "protecting group" is used in the conventional chemical sense as a group which reversibly renders unreactive a functional group under certain conditions of a desired reaction, as taught, for example, in Greene, et al., "Protective Groups in Organic Synthesis," John Wiley and Sons, Second Edition, 1991. After the desired reaction, protecting groups may be removed to deprotect the protected functional group. All protecting groups should be removable (and hence, labile) under conditions which do not degrade a substantial proportion of the molecules being synthesized. In contrast to a protecting group, a "capping group" permanently binds to a segment of a molecule to prevent any further chemical transformation of that segment. It should be noted that the functionality protected by the protecting group may or may not be a part of what is referred to as the protecting group.

A "hydroxyl protecting group" or "O-protecting group" refers to a protecting group where the protected group is a hydroxyl. A "reactive-site hydroxyl" is the terminal 5'-hydroxyl during 3'-5' polynucleotide synthesis, or the 3'-hydroxyl during 5'-3' polynucleotide synthesis. A "free reactive-site hydroxyl" is a reactive-site hydroxyl that is available to react to form an internucleotide bond (e.g. with a phosphoramidite functional group) during polynucleotide synthesis.

The term "deprotecting simultaneously" refers to a process which aims at removing different protecting groups in the same process and performed substantially concurrently or concurrently. However, as used herein, this term does not imply that the deprotection of the different protecting groups occur at exactly the same time or with the same rate or same kinetics.

A "phospho" group includes a phosphodiester, phosphotriester, and H-phosphonate groups. In the case of either a phospho or phosphite group, a chemical moiety other than a substituted 5-membered furyl ring may be attached to O of the phospho or phosphite group which links between the furyl ring and the P atom.

The term "phosphoramidite group" refers to a group comprising the structure —P—$(OR^{13})(NR^{14}R^{15})$, wherein each of $R^{13}$, $R^{14}$, and $R^{15}$ is independently a hydrocarbyl, substituted hydrocarbyl, heterocycle, substituted heterocycle, aryl or substituted aryl. In some embodiments, $R^{13}$, $R^{14}$, and $R^{15}$ may be selected from lower alkyls, lower aryls, and substituted lower alkyls and lower aryls (preferably substituted with structures containing up to 18, 16, 14, 12, 11, 10, 9, 8, 7, 6, 5, 4, 3 or 2 carbons). In some embodiments, $R^{13}$ is 2-cyanoethyl or methyl, and either or both of $R^{14}$ and $R^{15}$ is isopropyl. $R^{14}$ and $R^{15}$ can optionally be cyclically connected.

The term "alkyl" as used herein, unless otherwise specified, refers to a saturated straight chain, branched or cyclic hydrocarbon group of 1 to 24, typically 1-12, carbon atoms, such as methyl, ethyl, n-propyl, isopropyl, n-butyl, isobutyl, t-butyl, pentyl, cyclopentyl, isopentyl, neopentyl, hexyl, isohexyl, cyclohexyl, 3-methylpentyl, 2,2-dimethylbutyl, and 2,3-dimethylbutyl. The term "lower alkyl" intends an alkyl group of one to six carbon atoms, and includes, for example, methyl, ethyl, n-propyl, isopropyl, n-butyl, isobutyl, t-butyl, pentyl, cyclopentyl, isopentyl, neopentyl, hexyl, isohexyl, cyclohexyl, 3-methylpentyl, 2,2-dimethylbutyl, and 2,3-dimethylbutyl. The term "cycloalkyl" refers to cyclic alkyl groups such as cyclopropyl, cyclobutyl, cyclopentyl, cyclohexyl, cycloheptyl and cyclooctyl.

Moreover, the term "alkyl" includes "modified alkyl", which references an alkyl group having from one to twenty-four carbon atoms, and further having additional groups, such as one or more linkages selected from ether-, thio-, amino-, phosphor oxo-, ester-, and amido-, and/or being substituted with one or more additional groups including lower alkyl, aryl, alkoxy, thioalkyl, hydroxyl, amino, sulfonyl, thio, mercapto, imino, halo, cyano, nitro, nitroso, azide, carboxy, sulfide, sulfone, sulfoxy, phosphoryl, silyl, silyloxy, and boronyl. Similarly, the term "lower alkyl" includes "modified lower alkyl", which references a group having from one to eight carbon atoms and further having additional groups, such as one or more linkages selected from ether-, thio-, amino-, phosphor keto-, ester-, and amido-, and/or being substituted with one or more groups including lower alkyl; aryl, alkoxy, thioalkyl, hydroxyl, amino, sulfonyl, thio, mercapto, imino, halo, cyano, nitro, nitroso, azide, carboxy, sulfide, sulfone, sulfoxy, phosphoryl, silyl, silyloxy, and boronyl. The term "alkoxy" as used herein refers to a substituent —O—R wherein R is alkyl as defined above. The term "lower alkoxy" refers to such a group wherein R is lower alkyl. The term "thioalkyl" as used herein refers to a substituent —S—R wherein R is alkyl as defined above.

The term "alkenyl" as used herein, unless otherwise specified, refers to a branched, unbranched or cyclic (e.g. in the case of C5 and C6) hydrocarbon group of 2 to 24, typically 2 to 12, carbon atoms containing at least one double bond, such as ethenyl, vinyl, allyl, octenyl, decenyl, and the like. The term "lower alkenyl" intends an alkenyl group of two to eight carbon atoms, and specifically includes vinyl and allyl. The term "cycloalkenyl" refers to cyclic alkenyl groups.

The term "alkynyl" as used herein, unless otherwise specified, refers to a branched or unbranched hydrocarbon group of 2 to 24, typically 2 to 12, carbon atoms containing at least one triple bond, such as acetylenyl, ethynyl, n-propynyl, isopropynyl, n-butynyl, isobutynyl, t-butynyl, octynyl, decynyl and the like. The term "lower alkynyl" intends an alkynyl group of two to eight carbon atoms, and includes, for example, acetylenyl and propynyl, and the term "cycloalkynyl" refers to cyclic alkynyl groups.

The term "hydrocarbyl" refers to alkyl, alkenyl or alkynyl. The term "substituted hydrocarbyl" refers to hydrocarbyl moieties having substituents replacing a hydrogen on one or more carbons of the hydrocarbon backbone. Such substituents may include, for example, a hydroxyl, a halogen, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclic, an aralkyl, or an aromatic or heteroaromatic moiety. It will be understood by those skilled in the art that the moieties substituted on the hydrocarbon chain may themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —CN, and the like. Cycloalkyls may be further substituted with alkyls, alkenyls, alkoxys, alkylthios, aminoalkyls, carbonyl-substituted alkyls, —CN, and the like.

The term "alkoxy" means an alkyl group linked to oxygen and may be represented by the formula: R—O—, wherein R represents the alkyl group. An example is the methoxy group $CH_3O$—.

The term "aryl" refers to 5-, 6-, and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The term "aryl" also includes polycyclic ring systems having two or more cyclic rings in which two or more carbons are common to two adjoining rings (the rings are "fused rings") wherein at least one of the rings is aromatic (e.g., the other cyclic rings may be cycloalkyls, cycloalkenyls, cycloalkynyls, aryls, and/or heterocycles). A "lower aryl" contains up to 18 carbons, such as up to 14, 12, 10, 8 or 6 carbons.

The aromatic rings may be substituted at one or more ring positions with such substituents as described above for substituted hydrocarbyls, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclic, aromatic or heteroaromatic moieties, —$CF_3$, —CN, or the like.

The terms "halogen" and "halo" refer to fluorine, chlorine, bromine, or iodine.

"Linkage" as used herein refers to a first moiety bonded to two other moieties, wherein the two other moieties are linked via the first moiety. Typical linkages include ether (—O—), oxo (—C(O)—), amino (—NH—), amido (—N—C(O)—), thio (—S—), phospho (—P—), ester (—O—C(O)—).

"Functionalized" references a process whereby a material is modified to have a specific moiety bound to the material, e.g. a molecule or substrate is modified to have the specific moiety; the material (e.g. molecule or support) that has been so modified is referred to as a functionalized material (e.g. functionalized molecule or functionalized support).

The term "substituted" as used to describe chemical structures, groups, or moieties, refers to the structure, group, or moiety comprising one or more substituents. As used herein, in cases in which a first group is "substituted with" a second group, the second group is attached to the first group whereby a moiety of the first group (typically a hydrogen) is replaced by the second group.

"Substituent" references a group that replaces another group in a chemical structure. Typical substituents include nonhydrogen atoms (e.g. halogens), functional groups (such as, but not limited to amino, sulfhydryl, carbonyl, hydroxyl, alkoxy, carboxyl, silyl, silyloxy, phosphate and the like), hydrocarbyl groups, and hydrocarbyl groups substituted with one or more heteroatoms. Exemplary substituents include alkyl, lower alkyl, aryl, aralkyl, lower alkoxy, thioalkyl, hydroxyl, thio, mercapto, amino, imino, halo, cyano, nitro, nitroso, azide, carboxy, sulfide, sulfone, sulfoxy, phosphoryl, silyl, silyloxy, boronyl, and modified lower alkyl.

Hyphens, or dashes are used at various points throughout this specification to indicate attachment, e.g. where two named groups are immediately adjacent to a dash in the text, this indicates that the two named groups area attached to each other. Similarly, a series of named groups with dashes between each of the named groups in the text indicated the named groups are attached to each other in the order shown. Also, a single named group adjacent a dash in the text indicates that the named group is typically attached to some other, unnamed group. In some embodiments, the attachment indicated by a dash may be, e.g., a covalent bond between the adjacent named groups. At various points throughout the specification, a group may be set forth in the text with or without an adjacent dash, (e.g. amido or amido-, further e.g. alkyl or alkyl-, yet further Lnk, Lnk- or -Lnk-) where the context indicates the group is intended to be (or has the potential to be) bound to another group; in such cases, the identity of the group is denoted by the group name (whether or not there is an adjacent dash in the text). Note that where context indicates, a single group may be attached to more than one other group (e.g., where a linkage is intended, such as linking groups).

Dashed lines (e.g., ------) are used throughout the specification adjacent to named groups to indicate attachment to some other, unnamed group.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present, and, thus, the description includes structures wherein a non-hydrogen substituent is present and structures wherein a non-hydrogen substituent is not present. At various points herein, a moiety may be described as being present zero or more times: this is equivalent to the moiety being optional and includes embodiments in which the moiety is present and embodiments in which the moiety is not present. If the optional moiety is not present (is present in the structure zero times), adjacent groups described as linked by the optional moiety are linked to each other directly. Similarly, a moiety may be described as being either (1) a group linking two adjacent groups, or (2) a bond linking the two adjacent groups: this is equivalent to the moiety being optional and includes embodiments in which the moiety is present and embodiments in which the moiety is not present. If the optional moiety is not present (is present in the structure zero times), adjacent groups described as linked by the optional moiety are linked to each other directly.

"Bound" may be used herein to indicate direct or indirect attachment. In the context of chemical structures, "bound" (or "bonded") may refer to the existence of a chemical bond directly joining two moieties or indirectly joining two moieties (e.g. via a linking group or any other intervening portion of the molecule). The chemical bond may be a covalent bond, an ionic bond, a coordination complex, hydrogen bonding, van der Waals interactions, or hydrophobic stacking, or may exhibit characteristics of multiple types of chemical bonds. In certain instances, "bound" includes embodiments where the attachment is direct and also embodiments where the attachment is indirect. "Free," as used in the context of a moiety that is free, indicates that the moiety is available to react with or be contacted by other components of the solution in which the moiety is a part.

The term "assessing" includes any form of measurement, and includes determining if an element is present or not. The terms "determining", "measuring", "evaluating", "assessing" and "assaying" are used interchangeably and may include quantitative and/or qualitative determinations. Assessing may be relative or absolute. "Assessing the presence of" includes determining the amount of something present and/or determining whether it is present or absent.

"Isolated" or "purified" generally refers to isolation of a substance (compound, polynucleotide, protein, polypeptide, polypeptide, chromosome, etc.) such that the substance comprises a substantial portion of the sample in which it resides (excluding solvents), i.e. greater than the substance is typically found in its natural or un-isolated state. Typically, a substantial portion of the sample comprises at least about 1%, at least about 5%, at least about 10%, at least about 20%, at least about 30%, at least about 50%, preferably at least about 80%, or more preferably at least about 90% of the sample (excluding solvents). For example, a sample of isolated RNA will typically comprise at least about 5% total RNA, where percent is calculated in this context as mass (e.g. in micrograms) of total RNA in the sample divided by mass (e.g. in micrograms) of the sum of (total RNA+other constituents in the sample (excluding solvent)). Techniques for purifying polynucleotides and polypeptides of interest are well known in the art and include, for example, gel electrophresis, ion-exchange chromatography, affinity chromatography, flow sorting, and sedimentation according to density. In typical embodiments, one or more of the nucleotide composition(s) is in isolated form; more typically, all three are obtained in isolated form prior to use in the present methods.

The term "pre-determined" refers to an element whose identity is known prior to its use. For example, a "pre-determined sequence" is a sequence whose identity is known prior to the use or synthesis of the polynucleotide having the sequence. An element may be known by name, sequence, molecular weight, its function, or any other attribute or identifier.

"Upstream" as used herein refers to the 5' direction along a polynucleotide, e.g. an RNA molecule. "Downstream" refers to the 3' direction along the polynucleotide. "3'-" and "5'-" have their conventional meaning as known in the art.

DETAILED DESCRIPTION

Aspects of the invention include 2' protected nucleoside monomers that are protected at the 2' site with orthoester-type protecting groups. The 2' protected monomers also include a second, aryl carbonate-type, protecting group. Embodiments of the orthoester-type protecting groups include orthoester protecting groups as well as orthothioester protecting groups. Embodiments of the acyl carbonate-type protecting groups include acyl carbonate protecting groups as well as acyl thio-carbonate protecting groups. Aspects of the invention further include nucleic acids that include the protecting groups of the invention, as well as methods of synthesizing nucleic acids using the protecting groups of the invention.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It should be noted that, as is conventional in drawing some chemical structures, some of the hydrido groups are omitted from the drawn structures for clarity purposes, but should be understood to be present, e.g. where necessary to completely fill out the valence bonding of a carbon in a drawn structure.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Monomers Protected with Aryl Carbonate-Type Protecting Groups and Orthoester-Type Protecting Groups As summarized above, aspects of the invention include aryl carbonate-type hydroxyl protecting groups, orthoester-type hydroxyl protecting groups and monomers that include both types of protecting groups. The aryl carbonate-type hydroxyl protecting groups can be removed by reaction with nucleophiles, such as α-effect nucleophiles, which allow for mild deprotection conditions. The orthoester-type hydroxyl protecting groups can be removed under acidic conditions.

Some embodiments of the invention include nucleoside monomers that include an orthoester-type 2' hydroxyl protecting group and an acyl carbonate-type hydroxyl protecting group.

Embodiments of the invention include nucleoside monomers described by Formula (I):

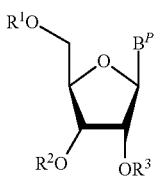

wherein:
$B^P$ is a protected or unprotected heterocycle;
one of $R^1$ or $R^2$ is an aryl carbonate-type protecting group; and the other of $R^1$ or $R^2$ is selected from hydrogen, a protecting group, and a phosphoramidite group; and
$R^3$ is an orthoester-type protecting group.

As described above with regard to structure (I), the $B^P$ group is a protected or non-protected heterocycle. The heterocycle may be selected from the naturally occurring purine and pyrimidine bases, e.g., adenine (A), thymine (T), cytosine (C), guanine (G), or uracil (U), or modified purine and pyrimidine bases, and common analogs, e.g. such as are recited herein. Certain purine or pyrimidine analogs that are contemplated in this context include those described in U.S. patent application Ser. No. 10/324,409 entitled "Method of Producing Nucleic Acid Molecules with Reduced Secondary Structure", filed on Dec. 18, 2002; and also those described in U.S. patent application Ser. No. 09/358,141, now abandoned, entitled "Method of Producing Nucleic Acid Molecules with Reduced Secondary Structure", filed on Jul. 20, 1999.

In some embodiments, the heterocycle is selected from 1-methyladenine, 2-methyladenine, N6-methyladenine, N6-isopentyladenine, 2-methylthio-N6-isopentyladenine, N,N-dimethyladenine, 8-bromoadenine, 2-thiocytosine, 3-methylcytosine, 5-methylcytosine, 5-ethylcytosine, 4-acetylcytosine, 1-methylguanine, 2-methylguanine, 7-methylguanine, 2,2-dimethylguanine, 8-bromoguanine, 8-chloroguanine, 8-aminoguanine, 8-methylguanine, 8-thioguanine, 5-fluorouracil, 5-bromouracil, 5-chlorouracil, 5-iodouracil, 5-ethyluracil, 5-propyluracil, 5-methoxyuracil, 5-hydroxymethyluracil, 5-(carboxyhydroxymethyl)uracil, 5-(methylaminomethyl)uracil, 5-(carboxymethylaminomethyl)-uracil, 2-thiouracil, 5-methyl-2-thiouracil, 5-(2-bromovinyl)uracil, uracil-5-oxyacetic acid, uracil-5-oxyacetic acid methyl ester, pseudouracil, 1-methylpseudouracil, queosine, inosine, 1-methylinosine, hypoxanthine, xanthine, 2-aminopurine, 6-hydroxyaminopurine, 6-thiopurine and 2,6-diaminopurine.

In some embodiments, the heterocycle may have a protecting group, as is commonly known in the art of polynucleotide synthesis. In certain embodiments, a heterocycle protecting group selected from acetyl, difluoroacetyl, trifluoroacetyl, isobutyryl, benzoyl, 9-fluorenylmethoxycarbonyl, phenoxyacetyl, dimethylformamidine, or N,N-diphenyl carbamate is attached to the heterocycle.

In some embodiments, the aryl carbonate-type protecting groups have the structure:

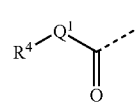

wherein the dashed line indicates the site at which the aryl carbonate-type hydroxyl protecting group having the structure (II) is bound to a 3' or 5' oxygen atom of a nucleoside or nucleoside residue, $Q^1$ is an oxygen or sulfur atom; and $R^4$ is an aryl group or a substituted aryl group.

In further embodiments, $R^4$ is a phenyl or substituted phenyl group. In certain of these embodiments, $R^4$ has the structure:

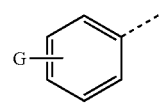

wherein:
the dashed line indicates the site at which $R^4$ is bound to $Q^1$;
G is one or more substituent groups each independently selected from lower hydrocarbyl, substituted lower hydrocarbyl, aryl, substituted aryl, halogen, cyano, amino, nitro, sulfate, alkyl thiolate, substituted alkyl thiolate, nitrate, and carbonate.

In certain embodiments, $R^4$ has the structure:

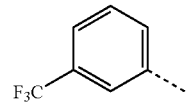

wherein the dashed line indicates the site at which $R^4$ is bound to $Q^1$.

In some embodiments, $R^3$ has the structure:

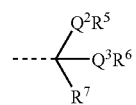

wherein:
the dashed line indicates the site at which $R^3$ is bound to the 2' oxygen of the nucleoside monomer;
$Q^2$ and $Q^3$ are each independently either a sulfur or oxygen atom;
$R^5$ and $R^6$ are each independently selected from hydrocarbyl, substituted hydrocarbyl, aryl, substituted aryl, or $R^5$ and R⁶, together with Q², Q³ and the carbon to which Q² and Q³ are attached are linked to form a heterocycle; and R⁷ is selected from hydrogen, hydrocarbyl, substituted hydrocarbyl, aryl, and substituted aryl.

In further embodiments, R⁵ and R⁶, together with Q², Q³ and the carbon to which Q² and Q³ are attached are linked to form a heterocycle. In certain of these embodiments, R³ has the structure:

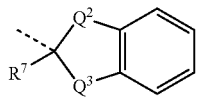

VI wherein the dashed line indicates the site at which R³ is bound to the 2' oxygen of the nucleoside monomer; and Q2 and Q³ are each independently either a sulfur or oxygen atom.

In certain other embodiments, R³ has the structure:

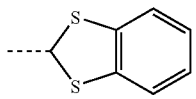

VII wherein the dashed line indicates the site at which R³ is bound to the 2' oxygen of the nucleoside monomer.

The following structures illustrate further embodiments of the present invention:

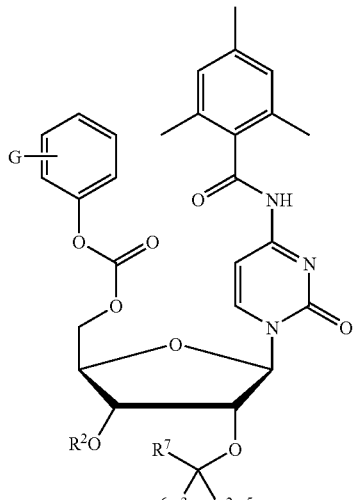

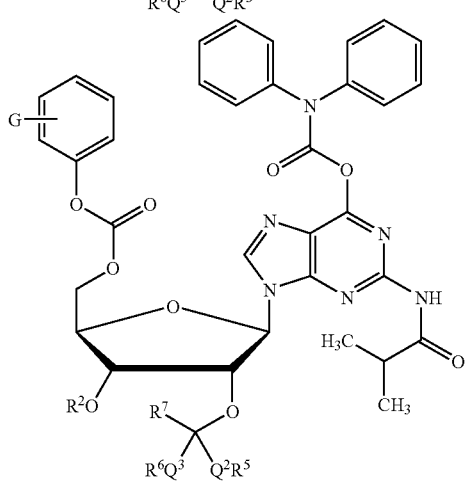

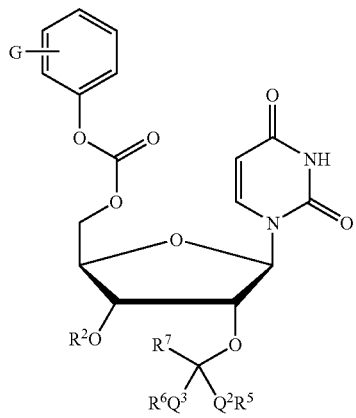

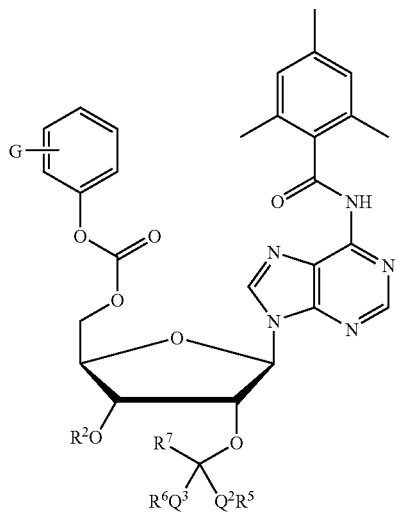

wherein G, Q², Q³, R², R⁵, R⁶, and R⁷ are as described above with respect to Formula (I), Formula (III), and Formula (V).

Additional embodiments of the present invention are shown below.

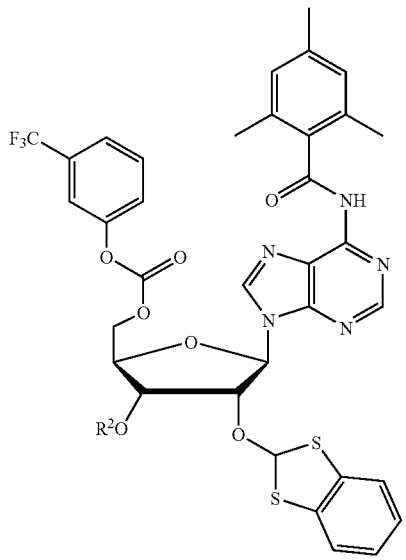

-continued

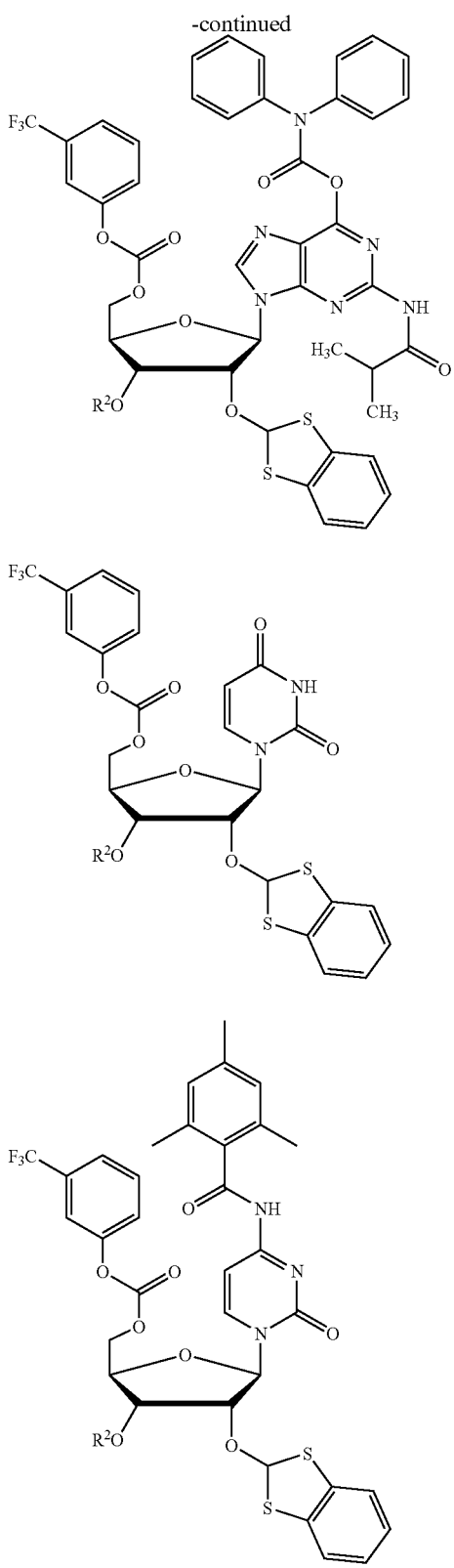

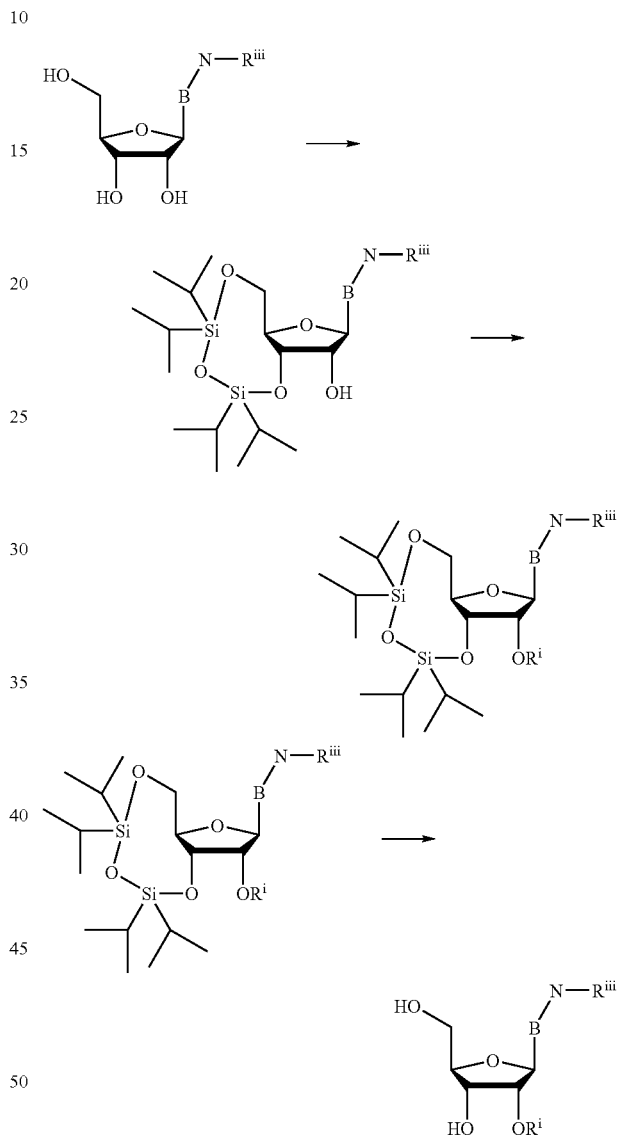

the composition under synthesis. The specific introduction on the 2'-hydroxyl (regioselectivity) is performed through the transient protection of the 5' and 3'-hydroxyl groups through the use if the Markewicz disilyloxane protecting group. The 1,3-tetraisopropyl disiloxane (TIPS) is a transient bidentate protecting group that is used to block the 5' and 3' hydroxyls simultaneously allowing the 2'-hydroxyl to be then regioselectively protected. The 1,3-tetraisopropyl disiloxane group is subsequently removed using a solution of fluoride ions.

Polymeric Synthesis Using Aryl Carbonate-Type Protecting Groups and Orthoester-Type Protecting Groups Aryl carbonate-type hydroxyl protected, 2' orthoester-type protected monomers of the invention find use in the synthesis of a variety of different types of polymers, including nucleic acids.

In particular embodiments, the novel nucleotide compositions may be employed in methods for synthesizing RNA. In some embodiments, the method provides for simultaneous oxidation of the internucleotide bond (e.g., the internucleoside phosphite triester linkage) and removal of the 3'- or 5'-hydroxyl-protecting group, making this process a new 2-step RNA synthesis. Certain embodiments of the invention are illustrated in Scheme I:

Embodiments of compositions in accordance with the present invention may be synthesized following a synthesis scheme such as those set out in FIG. 1. In certain embodiments, as illustrated below, synthesis employs the Markewicz TIPS reagent to localize protecting groups to the 2'-OH site of

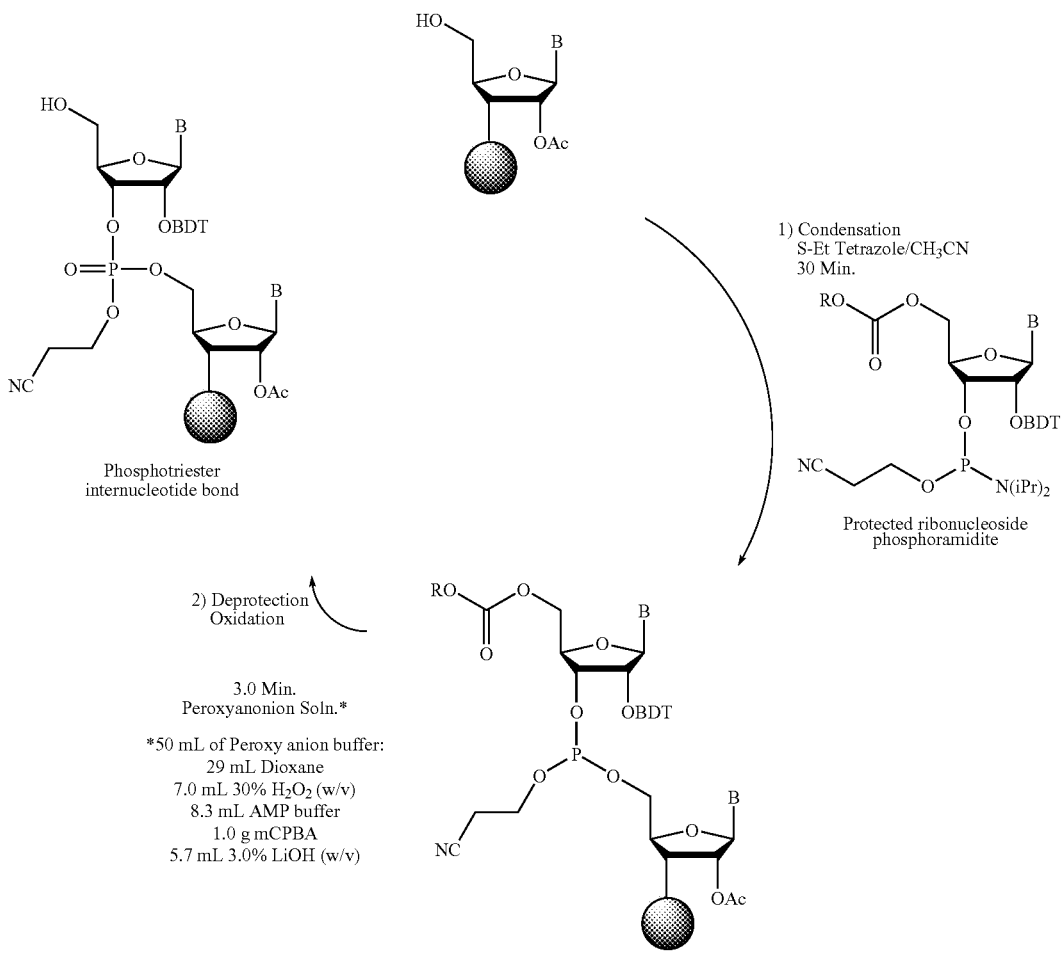

SCHEME I

In some embodiments, the coupling reaction is conducted under standard conditions used for the synthesis of oligonucleotides and conventionally employed with automated oligonucleotide synthesizers. In additional embodiments, as shown in the second step of the synthesis cycle shown in SCHEME I above, the product is treated with a combined deprotection/oxidation reagent to oxidize the newly formed internucleotide bond and to remove the hydroxyl protecting group at the 5' terminus. The resulting 5'-OH is then available to serve as the reactive-site hydroxyl for the next round of the synthesis cycle. Further, the method is useful in carrying out either 3'-to-5' synthesis or 5'-to-3' synthesis.

The deprotection/oxidation reaction essentially may be conducted under the reported conditions used for the synthesis of polynucleotides as described in, e.g. U.S. Pat. No. 6,222,030 to Dellinger et al.; U.S. Pat. No. 7,135,565 to Dellinger et al.; Seio et al. (2001) Tetrahedron Lett. 42 (49): 8657-8660. As will be appreciated by those of ordinary skill in the art, given the disclosure herein, the conditions for the deprotection/oxidation step may vary depending on the nature of the protecting groups used. In order to be compatible with the protecting group on the 2'-O as described herein, the conditions for the simultaneous deprotection and oxidation step (i.e. required conditions for release of the 3'- or 5'-hydroxyl protecting group) should be selected such that the protecting group on each of the 2'-O site(s) of the nascent polynucleotide remains stably attached to the nascent polynucleotide under conditions which provide for the deprotection of the 3'- or 5'-hydroxyl protecting group. In some embodiments, conditions for the deprotection/oxidation reaction include a pH in the neutral to moderately basic range. In further embodiments, the pH of the deprotection/oxidation reaction is at least about 6.0, including a pH of at least about 6.5, further including a pH of at least about 7.0, still further including a pH of at least about 7.5. In additional embodiments, the pH is less than about 12, including a pH of less than about 11, further including a pH of less than about 10.5, still further including a pH of less than about 10.

Certain embodiments utilize a combined deprotection/oxidation reagent which may be selected to provide particularly advantageous synthesis conditions and characteristics, as are described herein. In some embodiments, the combined deprotection/oxidation step provides for contacting the elongating polynucleotide chain with an alpha effect nucleophile under neutral or mildly basic aqueous conditions to remove the reactive site hydroxyl protecting group (e.g., the 5' terminus for synthesis in the 3' to 5' direction, or the 3' terminus for synthesis in the 5' to 3' direction) where that protecting group is labile under nucleophilic attack. The alpha effect nucleophile also oxidizes the newly formed phosphite triester linkage to give the phosphotriester linkage as shown in above SCHEME I.

The deprotection/oxidation reagent may be any compound or mixture of compounds that is compatible with the synthesis of polynucleotides and has the properties discussed herein. In some embodiments, the deprotection/oxidation reagent includes a concentration of an oxidant that is high enough to rapidly oxidize the newly formed phosphite internucleotide linkage. In certain embodiments, this concentration is at least 0.1% vol/vol, including at least 0.5% vol/vol, further including at least about 1.0% vol/vol, still further including at least about 3.0% vol/vol. In these embodiments, the concentration of the oxidant should be low enough to avoid appreciable (e.g. less than 1% per iteration of the synthesis cycle) amounts of oxidative destruction of the nucleobases or protected nucleobases. In certain embodiments, this concentration is less than 10% vol/vol, including less than 9% vol/vol, further including less than 7% vol/vol.

In some embodiments, the deprotection/oxidation reagent provides a source of a peroxyanion at neutral to mildly basic pH in the reaction mixture during the deprotection/oxidation reaction. The concentration of the peroxyanion will be related to the acid dissociation constant of the hydroperoxide species at equilibrium. The concentration of peroxyanion is in the range 0.01% to 99% of the total hydroperoxide concentration (i.e., sum of all hydroperoxide species, e.g., protonated and unprotonated forms), including the range 0.05% to 90% of the total hydroperoxide concentration, further including the range 0.1% to 50% of the total hydroperoxide concentration, still further including the range of 1.0% to 30% of the total hydroperoxide concentration.

In certain embodiments, the nucleophilic deprotection reagent that exhibits an alpha effect is a peroxide or a mixture of peroxides. In some embodiments, the pH at which the deprotection/oxidation reaction is conducted is generally in the range of about three pH units below the pKa of the nucleophilic deprotection reagent (that is, the pKa for formation of the corresponding peroxy anion) up to about three pH units above the pKa of the nucleophilic deprotection reagent. In further embodiments, the pH of the deprotection/oxidation reaction is in the range of about one pH unit below the pKa of the nucleophilic deprotection reagent up to about pH 11. In other embodiments, the pH will be the range that allows a high enough concentration of the peroxy anion to form, e.g., from about the pKa of the peroxide up to a pH of about 11. The peroxide may be either inorganic or organic. Suitable inorganic peroxides include those of the formula M+OOH—, where M+ is any counter ion, including for example H+, Li+, Na+, K+, Rb+, Cs+, or the like. In some embodiments, lithium peroxide or hydrogen peroxide and alkaline stabilized forms thereof are used. Suitable organic peroxides include those of the formula ROOH, where R is selected from the group consisting of alkyl, aryl, substituted alkyl, substituted aryl, and modified alkyl. More particularly, the organic peroxide will have the structure of Formula (XII), Formula (XIII), or Formula (XIV):

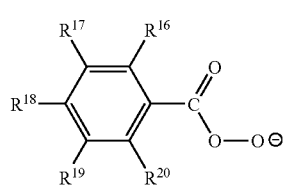

XII

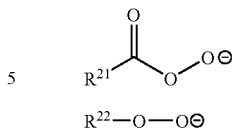

XIII

XIV in which $R^{13}$ through $R^{19}$ are independently selected from the group consisting of hydrido, hydrocarbyl, substituted hydrocarbyl, aryl, and substituted aryl. In some embodiments, the alpha-effect nucleophile is t-butyl-hydroperoxide or metachloroperoxybenzoic acid. For example, the m-chloroperoxybenzoic acid (mCPBA) peroxy anion has been found to be useful for removal of protecting groups on the reactive site hydroxyl.

As indicated in the above SCHEME I, the steps of the synthesis cycle can include a coupling step and a simultaneous deprotection/oxidation step. In an embodiment of a method of synthesizing a polynucleotide in accordance with the present invention, these steps of the synthesis cycle may be repeated multiple times to produce a polynucleotide having the desired sequence.

In some embodiments, after the series of coupling and deprotection/oxidation steps results in an oligonucleotide having a desired sequence and length, the resulting oligonucleotide undergoes a post-synthesis deprotection step, in which protected sites on the heterocycles and/or the 2'-oxygens are deprotected. For example, protecting groups bound to the heterocycles and/or the 2'-sites of the nucleotide subunits of the resulting nucleotide may be removed to provide a deprotected oligonucleotide.

Some embodiments in accordance with the present invention provide methods and compositions for post-synthesis RNA deprotection, particularly compositions used to remove the 2'-benzodithiolane (BDT) groups such as $HBF_4$/TEMED at pH 3.8 as depicted in SCHEME II below.

SCHEME II

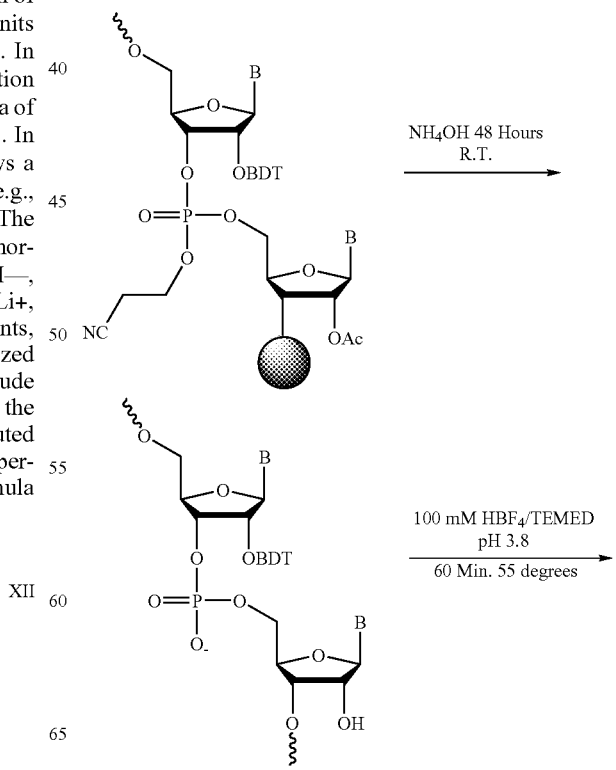

In certain embodiments of the present invention, the doubly protected monomers of the invention are used in the synthesis of ribonucleic acids, for example, in solid-phase or solution-phase synthesis of ribonucleic acids. Synthesis in accordance with the invention can be performed in either direction: e.g., from 3' to 5' or from 5' to 3'. For example, in the 3' to 5' direction, a first nucleoside monomer with a 5'-OH and a 3' protecting group is coupled with a second nucleoside monomer having a 3' phosphoramidite group and a 5' protecting group. The first nucleoside monomer is optionally bound to a solid support, e.g., where synthesis is carried out using solid phase synthesis protocols. Alternatively, this synthesis can be performed in solution.

After the coupling step, in which the 5'-OH and the 3'-phosphoramidite moieties condense to form a phosphite triester linkage and result in a dinucleotide, the dinucleotide is capped/oxidized, and the 5'-protecting group is removed (deprotection). The dinucleotide is then ready for coupling with another nucleoside monomer having a 3'-phosphoramidite group and a 5'-protecting group. These steps are repeated until the oligonucleotide reaches the desired length and/or sequence.

As such, aspects of the invention include methods of synthesizing nucleic acids that include the steps of providing a nucleoside residue having an unprotected hydroxyl group and a nucleoside monomer with a 2' orthoester-type hydroxyl protecting group and an aryl carbonate-type protecting group; and contacting the nucleoside residue and the 2' orthoester-type protected nucleoside monomer under conditions sufficient to covalently bond the 2' orthoester-type protected nucleoside monomer to the nucleoside residue to produce a nucleic acid. The above sections describe a single monomer addition step of the synthesis protocol, where the above process is reiterated with additional monomers as desired to produce a polymer of desired length and sequence. As reviewed above, between each monomer addition step, the process may include exposing the nucleic acid to an oxidizing and deprotecting agent.

In certain embodiments, the 2' orthoester-type protected nucleoside monomer has the structure of Formula (I), with the same limitations on Formula (I) as described above.

In additional embodiments, the aryl carbonate protecting group of the 2' orthoester-type protected nucleoside monomer has the structure of Formula (II), with the same limitations on Formula (II) as described above.

In further embodiments, $R^4$ is an aryl or a substituted aryl group. In certain embodiments, $R^4$ is a phenyl or substituted phenyl group. In certain of these embodiments, $R^4$ has the structure of Formula (III), with the same limitations on Formula (III) as described above.

In certain embodiments, $R^4$ has the structure of Formula (IV), wherein the dashed line indicates the site at which $R^4$ is bound to $Q^1$.

In other embodiments, $R^3$ has the structure of Formula (V), with the same limitations on Formula (V) as described above.

In certain of these embodiments, $R^5$ and $R^6$, together with $Q^2$, $Q^3$ and the carbon to which $Q^2$ and $Q^3$ are attached are linked to form a heterocycle. In certain embodiments, $R^3$ has the structure of Formula (VI), with the same limitations on Formula (VI) as described above.

In certain other embodiments, $R^3$ has the structure of Formula (VII), wherein the dashed line indicates the site at which $R^3$ is bound to the 2' oxygen of the nucleoside monomer.

In further embodiments, the method of making nucleic acids additionally comprises removing the 2' orthoester-type protecting groups from the product nucleic acid by incubating the nucleic acid with an acid.

In additional embodiments, $R^2$ is an aryl carbonate protecting group, and $R^1$ has the structure of Formula (IX),

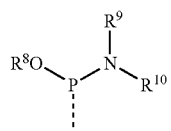

IX wherein $R^8$, $R^9$, and $R^{10}$ are each independently selected from the group consisting of hydrocarbyls, substituted hydrocarbyls, aryls and substituted aryls.

In other embodiments, $R^1$ is an aryl carbonate protecting group, and R has the structure of Formula (IX), with the same limitations on Formula (IX) as described above.

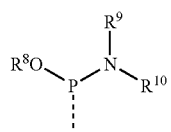

IX

Nucleic Acid Products

Aspects of the invention further include the nucleic acid products of the methods of invention. The nucleic acid products, e.g., RNA, of the methods of the invention may vary in size, ranging in certain embodiments from 2 to 200 or more monomeric units in length, such as 2 to 100 or more monomeric units in length, including 2 to 50 or more monomeric units in length. In certain embodiments, the size of the product nucleic acids ranges from 2 to 25 monomeric units in length, e.g., 15 to 25 monomeric units in length, such as 17 to 23 monomeric units in length, including 19, 20, 21, or 22 monomeric units in length.

In some embodiments, nucleic acid products of the invention have the structure of Formula (X):

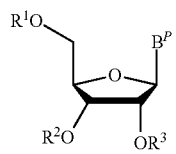

X wherein:
$B^P$ is a protected or unprotected heterocycle;
one of $R^1$ or $R^2$ is an aryl carbonate-type protecting group;
and the other of $R^1$ or $R^2$ has the structure of Formula (XI):

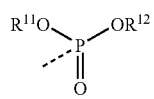

XI wherein:
$R^{11}$ is selected from the group consisting of hydrogen, hydrocarbyls, substituted hydrocarbyls, aryls, and substituted aryls;
$R^{12}$ is a nucleoside residue;
and $R^3$ is an orthoester-type protecting group.

In additional embodiments, the aryl carbonate-type protecting group has the structure of Formula (II), with the same limitations on Formula (II) as described above.

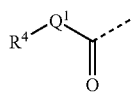

II

In certain embodiments, $R^4$ is a phenyl or substituted phenyl group. In certain of these embodiments, $R^4$ has the structure of Formula (III), with the same limitations on Formula (III) as described above.

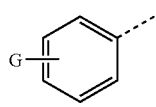

III

In certain other embodiments, $R^4$ has the structure of Formula (IV),

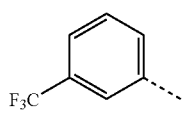

IV wherein the dashed line indicates the site at which $R^4$ is bound to $Q^1$.

In other embodiments, $R^3$ has the structure of Formula (V), with the same limitations on Formula (V) as described above.

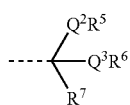

V

In certain embodiments, $R^5$ and $R^6$, together with $Q^2$, $Q^3$ and the carbon to which $Q^2$ and $Q^3$ are attached are linked to form a heterocycle. In certain of these embodiments, $R^3$ has the structure of Formula (VI), with the same limitations on Formula (VI) as described above.

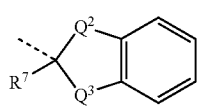

VI

In certain other embodiments, $R^3$ has the structure of Formula (VII),

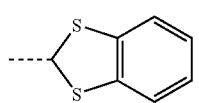

VII wherein the dashed line indicates the site at which $R^3$ is bound to the 2' oxygen of the nucleoside monomer.

Applications

The product nucleic acids produced in accordance with methods of the invention find use in a variety of applications, including research, diagnostic and therapeutic applications. For example, the product nucleic acids find use in research applications, e.g., as probes, primers, etc. With respect to diagnostic applications, the product nucleic acids may also find use as probes, primers, or other agents employed in diagnostic protocols. With respect to therapeutic applications, the product nucleic acids find use as any DNA, RNA or other nucleic acid therapeutic, such as antisense nucleic acids, in gene therapy applications, interfering RNA (i.e., iRNA or RNAi) applications, etc.

Depending on the application for which the nucleic acids are synthesized, the nucleic acids may or may not be modified in some manner following their synthesis. As such, in certain embodiments the product nucleic acids are not further modified following synthesis. In yet other embodiments, the nucleic acids are modified in some manner following their synthesis.

A variety of different modifications may be made to the product nucleic acids as desired. For example, where the product nucleic acids are interfering ribonucleic acids (iRNA), a variety of post-synthesis modifications may be desirable. The iRNA agent can be further modified so as to be attached to a ligand that is selected to improve stability, distribution or cellular uptake of the agent, e.g., cholesterol. The following post-synthesis modifications are described for convenience primarily in terms of iRNA embodiments. However, such modifications are readily adapted to DNA embodiments and the following description encompasses such embodiments as well.

The following modifications may be made before or after cleavage of the nucleic acid from the support, as desired.

Unmodified RNA refers to a molecule in which the components of the nucleic acid, namely sugars, bases, and phosphate moieties, are the same or essentially the same as that which occur in nature, e.g., as occur naturally in the human body. The art has referred to rare or unusual, but naturally occurring, RNAs as modified RNAs, see, e.g., Limbach et al., (1994) Nucleic Acids Res. 22: 2183-2196. Such rare or unusual RNAs, often termed modified RNAs (apparently because these are typically the result of a post-transcriptional modification) are within the term unmodified RNA, as used herein. Modified RNA as used herein refers to a molecule in which one or more of the components of the nucleic acid, namely sugars, bases, and phosphate moieties, are different from that which occurs in nature, e.g., different from that which occurs in the human body. While they are referred to as modified "RNAs," they will of course, because of the modification, include molecules which are not RNAs. Nucleoside surrogates are molecules in which the ribophosphate backbone is replaced with a non-ribophosphate construct that allows the bases to the presented in the correct spatial relationship such that hybridization is substantially similar to what is seen with a ribophosphate backbone, e.g., non-charged mimics of the ribophosphate backbone. Examples of each of the above are discussed herein.

Modifications described herein can be incorporated into any double-stranded RNA and RNA-like molecule described herein, e.g., an iRNA agent. It may be desirable to modify one or both of the antisense and sense strands of an iRNA agent. As nucleic acids are polymers of subunits or monomers, many of the modifications described below occur at a position which is repeated within a nucleic acid, e.g., a modification of a base, or a phosphate moiety, or the non-linking 0 of a phosphate moiety. In some cases the modification will occur at all of the subject positions in the nucleic acid but in many, and in fact in most, cases it will not. By way of example, a modification may only occur at a 3' or 5' terminal position, may only occur in a terminal region, e.g. at a position on a terminal nucleotide or in the last 2, 3, 4, 5, or 10 nucleotides of a strand. A modification may occur in a double strand region, a single strand region, or in both. For example, a phosphorothioate modification at a non-linking 0 position may only occur at one or both termini, may only occur in a terminal regions, e.g., at a position on a terminal nucleotide or in the last 2, 3, 4, 5, or 10 nucleotides of a strand, or may occur in double strand and single strand regions, particularly at termini. Similarly, a modification may occur on the sense strand, antisense strand, or both. In some cases, the sense and antisense strand will have the same modifications or the same class of modifications, but in other cases the sense and antisense strand will have different modifications, e.g., in some cases it may be desirable to modify only one strand, e.g. the sense strand.

Two prime objectives for the introduction of modifications into iRNA agents is their stabilization towards degradation in biological environments and the improvement of pharmacological properties, e.g., pharmacodynamic properties, which are further discussed below. Other suitable modifications to a sugar, base, or backbone of an iRNA agent are described in PCT Application No. PCT/US2004/01193, filed Jan. 16, 2004. An iRNA agent can include a non-naturally occurring base, such as the bases described in PCT Application No. PCT/US2004/011822, filed Apr. 16, 2004. An iRNA agent can include a non-naturally occurring sugar, such as a non-carbohydrate cyclic carrier molecule. Exemplary features of non-naturally occurring sugars for use in iRNA agents are described in PCT Application No. PCT/US2004/11829 filed Apr. 16, 2003.

An iRNA agent can include an internucleotide linkage (e.g., the chiral phosphorothioate linkage) useful for increasing nuclease resistance. In addition, or in the alternative, an iRNA agent can include a ribose mimic for increased nuclease resistance. Exemplary internucleotide linkages and ribose mimics for increased nuclease resistance are described in PCT Application No. PCT/US2004/07070 filed on Mar. 8, 2004.

An iRNA agent can include ligand-conjugated monomer subunits and monomers for oligonucleotide synthesis. Exemplary monomers are described in U.S. application Ser. No. 10/916,185, filed on Aug. 10, 2004. An iRNA agent can have a ZXY structure, such as is described in PCT Application No. PCT/US2004/07070 filed on Mar. 8, 2004. An iRNA agent can be complexed with an amphipathic moiety. Exemplary amphipathic moieties for use with iRNA agents are described in PCT Application No. PCT/US2004/07070 filed on Mar. 8, 2004.

In another embodiment, the iRNA agent can be complexed to a delivery agent that features a modular complex. The complex can include a carrier agent linked to one or more of (such as two or more, including all three of): (a) a condensing agent (e.g., an agent capable of attracting, e.g., binding, a nucleic acid, e.g., through ionic or electrostatic interactions); (b) a fusogenic agent (e.g., an agent capable of fusing and/or being transported through a cell membrane); and (c) a targeting group, e.g., a cell or tissue targeting agent, e.g., a lectin, glycoprotein, lipid or protein, e.g., an antibody, that binds to a specified cell type. iRNA agents complexed to a delivery agent are described in PCT Application No. PCT/US2004/07070 filed on Mar. 8, 2004.

An iRNA agent can have non-canonical pairings, such as between the sense and antisense sequences of the iRNA duplex. Exemplary features of non-canonical iRNA agents are described in PCT Application No. PCT/US2004/07070 filed on Mar. 8, 2004.

An iRNA agent can have enhanced resistance to nucleases. For increased nuclease resistance and/or binding affinity to the target, an iRNA agent, e.g., the sense and/or antisense strands of the iRNA agent, can include, for example, 2'-modified ribose units and/or phosphorothioate linkages. For example, the 2' hydroxyl group (OH) can be modified or replaced with a number of different "oxy" or "deoxy" substituents.

Examples of "oxy"-2' hydroxyl group modifications include alkoxy or aryloxy (OR, e.g., R=H, alkyl, cycloalkyl, aryl, aralkyl, heteroaryl or sugar); polyethyleneglycols (PEGs), $O(CH_2CH_2O)_nCH_2CH_2OR$; "locked" nucleic acids (LNA) in which the 2' hydroxyl is connected, e.g., by a methylene bridge, to the 4' carbon of the same ribose sugar; O-AMINE and aminoalkoxy, $O(CH_2)_n$AMINE, (e.g., AMINE=$NH_2$; alkylamino, dialkylamino, heterocyclyl amino, arylamino, diaryl amino, heteroaryl amino, or diheteroaryl amino, ethylene diamine, polyamino). It is noteworthy that oligonucleotides containing only the methoxyethyl group (MOE), ($OCH_2CH_2OCH_3$, a PEG derivative), exhibit nuclease stabilities comparable to those modified with the robust phosphorothioate modification.

"Deoxy" modifications include hydrogen (i.e. deoxyribose sugars, which are of particular relevance to the overhang portions of partially ds RNA); halo (e.g., fluoro); amino (e.g. $NH_2$; alkylamino, dialkylamino, heterocyclyl, arylamino, diaryl amino, heteroaryl amino, diheteroaryl amino, or amino acid); $NH(CH_2CH_2NH)_nCH_2CH_2$-AMINE (AMINE=$NH_2$; alkylamino, dialkylamino, heterocyclyl amino, arylamino, diaryl amino, heteroaryl amino, or diheteroaryl amino), —NHC(O)R(R=alkyl, cycloalkyl, aryl, aralkyl, heteroaryl or sugar), cyano; mercapto; alkyl-thio-alkyl; thioalkoxy; and alkyl, cycloalkyl, aryl, alkenyl and alkynyl, which may be optionally substituted with e.g., an amino functionality.

One way to increase resistance is to identify cleavage sites and modify such sites to inhibit cleavage, as described in U.S. Application No. 60/559,917, filed on May 4, 2004. For example, the dinucleotides 5'-UA-3',5'-UG-3',5'-CA-3',5'-UU-3', or 5'-CC-3' can serve as cleavage sites. Enhanced nuclease resistance can therefore be achieved by modifying the 5' nucleotide, resulting, for example, in at least one 5'-uridine-adenine-3' (5'-UA-3') dinucleotide wherein the uridine is a 2'-modified nucleotide; at least one 5'-uridine-guanine-3' (5'-UG-3') dinucleotide, wherein the 5'-uridine is a 2'-modified nucleotide; at least one 5'-cytidine-adenine-3' (5'-CA-3') dinucleotide, wherein the 5'-cytidine is a 2'-modified nucleotide; at least one 5'-uridine-uridine-3' (5'-UU-3') dinucleotide, wherein the 5'-uridine is a 2'-modified nucleotide; or at least one 5'-cytidine-cytidine-3' (5'-CC-3') dinucleotide, wherein the 5'-cytidine is a 2'-modified nucleotide. The iRNA agent can include at least 2, at least 3, at least 4 or at least 5 of such dinucleotides. In certain embodiments, all the pyrimidines of an iRNA agent carry a 2'-modification, and the iRNA agent therefore has enhanced resistance to endonucleases.

To maximize nuclease resistance, the 2' modifications can be used in combination with one or more phosphate linker modifications (e.g., phosphorothioate). The so-called "chimeric" oligonucleotides are those that contain two or more different modifications.

The inclusion of furanose sugars in the oligonucleotide backbone can also decrease endonucleolytic cleavage. An iRNA agent can be further modified by including a 3' cationic group, or by inverting the nucleoside at the 3'-terminus with a 3'-3' linkage. In another alternative, the 3'-terminus can be blocked with an aminoalkyl group, e.g., a 3'C5-aminoalkyl dT. Other 3' conjugates can inhibit 3'-5' exonucleolytic cleavage. While not being bound by theory, a 3' conjugate, such as naproxen or ibuprofen, may inhibit exonucleolytic cleavage by sterically blocking the exonuclease from binding to the 3'-end of the oligonucleotide. Even small alkyl chains, aryl groups, or heterocyclic conjugates or modified sugars (D-ribose, deoxyribose, glucose etc.) can block 3'-5'-exonucleases.

Similarly, 5' conjugates can inhibit 5'-3' exonucleolytic cleavage. While not being bound by theory, a 5' conjugate, such as naproxen or ibuprofen, may inhibit exonucleolytic cleavage by sterically blocking the exonuclease from binding to the 5'-end of the oligonucleotide. Even small alkyl chains, aryl groups, or heterocyclic conjugates or modified sugars (D-ribose, deoxyribose, glucose etc.) can block 3'-5'-exonucleases.

An iRNA agent can have increased resistance to nucleases when a duplexed iRNA agent includes a single-stranded nucleotide overhang on at least one end. In some embodiments, the nucleotide overhang includes 1 to 4 unpaired nucleotides, in other embodiments 2 to 3 unpaired nucleotides. In one embodiment, the unpaired nucleotide of the single-stranded overhang that is directly adjacent to the terminal nucleotide pair contains a purine base, and the terminal nucleotide pair is a G-C pair, or at least two of the last four complementary nucleotide pairs are G-C pairs. In further embodiments, the nucleotide overhang may have 1 or 2 unpaired nucleotides, and in an exemplary embodiment the nucleotide overhang is 5'-GC-3'. In certain embodiments, the nucleotide overhang is on the 3'-end of the antisense strand. In one embodiment, the iRNA agent includes the motif 5'-CGC-3' on the 3'-end of the antisense strand, such that a 2-nucleotide overhang 5'-GC-3' is formed.

Thus, an iRNA agent can include modifications so as to inhibit degradation, e.g., by nucleases, e.g., endonucleases or exonucleases, found in the body of a subject. These monomers are referred to herein as NRMs, or Nuclease Resistance promoting Monomers, the corresponding modifications as NRM modifications. In many cases these modifications will modulate other properties of the iRNA agent as well, e.g., the ability to interact with a protein, e.g., a transport protein, e.g., serum albumin, or a member of the RISC, or the ability of the first and second sequences to form a duplex with one another or to form a duplex with another sequence, e.g., a target molecule.

One or more different NRM modifications can be introduced into an iRNA agent or into a sequence of an iRNA agent. An NRM modification can be used more than once in a sequence or in an iRNA agent.

NRM modifications include some which can be placed only at the terminus and others which can go at any position. Some NRM modifications that can inhibit hybridization may be used only in terminal regions, and not at the cleavage site or in the cleavage region of a sequence which targets a subject sequence or gene, particularly on the antisense strand. They can be used anywhere in a sense strand, provided that sufficient hybridization between the two strands of the ds iRNA agent is maintained. In some embodiments it is desirable to put the NRM at the cleavage site or in the cleavage region of a sense strand, as it can minimize off-target silencing.

In certain embodiments, the NRM modifications will be distributed differently depending on whether they are comprised on a sense or antisense strand. If on an antisense strand, modifications which interfere with or inhibit endonuclease cleavage should not be inserted in the region which is subject to RISC mediated cleavage, e.g., the cleavage site or the cleavage region (As described in Elbashir et al., 2001, Genes and Dev. 15: 188, hereby incorporated by reference). Cleavage of the target occurs about in the middle of a 20 or 21 nucleotide antisense strand, or about 10 or 11 nucleotides upstream of the first nucleotide on the target mRNA which is complementary to the antisense strand. As used herein cleavage site refers to the nucleotides on either side of the site of cleavage, on the target mRNA or on the iRNA agent strand which hybridizes to it. Cleavage region means the nucleotides within 1, 2, or 3 nucleotides of the cleavage site, in either direction.

Such modifications can be introduced into the terminal regions, e.g., at the terminal position or with 2, 3, 4, or 5 positions of the terminus, of a sequence which targets or a sequence which does not target a sequence in the subject.

The properties of an iRNA agent, including its pharmacological properties, can be influenced and tailored, for example, by the introduction of ligands, e.g. tethered ligands. A wide variety of entities, e.g., ligands, can be tethered to an iRNA agent, e.g., to the carrier of a ligand-conjugated monomer subunit. Examples are described below in the context of a ligand-conjugated monomer subunit but that is only preferred, entities can be coupled at other points to an iRNA agent.

Of interest are ligands, which are coupled, e.g., covalently, either directly or indirectly via an intervening tether, to the carrier. In certain embodiments, the ligand is attached to the carrier via an intervening tether. The ligand or tethered ligand may be present on the ligand-conjugated monomer when the ligand-conjugated monomer is incorporated into the growing strand. In some embodiments, the ligand may be incorporated into a "precursor" ligand-conjugated monomer subunit after a "precursor" ligand-conjugated monomer subunit has been incorporated into the growing strand. For example, a monomer having, e.g., an amino-terminated tether, e.g., TAP-$(CH_2)_nNH_2$ may be incorporated into a growing sense or antisense strand. In a subsequent operation, i.e., after incorporation of the precursor monomer subunit into the strand, a ligand having an electrophilic group, e.g., a pentafluorophenyl ester or aldehyde group, can subsequently be attached to the precursor ligand-conjugated monomer by coupling the electrophilic group of the ligand with the terminal nucleophilic group of the precursor ligand-conjugated monomer subunit tether.

In certain embodiments, a ligand alters the distribution, targeting or lifetime of an iRNA agent into which it is incorporated. In preferred embodiments a ligand provides an enhanced affinity for a selected target, e.g., molecule, cell or cell type, compartment, e.g., a cellular or organ compartment, tissue, organ or region of the body, as, e.g., compared to a species absent such a ligand.

Ligands of interest can improve transport, hybridization, and specificity properties and may also improve nuclease resistance of the resultant natural or modified oligoribonucleotide, or a polymeric molecule comprising any combination of monomers described herein and/or natural or modified ribonucleotides. Ligands in general can include therapeutic modifiers, e.g., for enhancing uptake; diagnostic compounds or reporter groups e.g., for monitoring distribution; cross-linking agents; nuclease-resistance conferring moieties; and natural or unusual nucleobases. General examples include lipophilic moleculeses, lipids, lectins, steroids (e.g., uvaol, hecigenin, diosgenin), terpenes (e.g., triterpenes, e.g., sarsasapogenin, Friedelin, epifriedelanol derivatized lithocholic acid), vitamins, carbohydrates (e.g., a dextran, pullulan, chitin, chitosan, inulin, cyclodextrin or hyaluronic acid), proteins, protein binding agents, integrin targeting molecules, polycationics, peptides, polyamines, and peptide mimics.

The ligand may be a naturally occurring or recombinant or synthetic molecule, such as a synthetic polymer, e.g., a synthetic polyamino acid. Examples of polyamino acids include polyamino acid is a polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacrylic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic moieties, e.g., cationic lipid, cationic porphyrin, quaternary salt of a polyamine, or an alpha helical peptide.

Ligands can also include targeting groups, e.g., a cell or tissue targeting agent, e.g., a thyrotropin, melanotropin, surfactant protein A, Mucin carbohydrate, a glycosylated polyaminoacid, transferrin, bisphosphonate, polyglutamate, polyaspartate, or an RGD peptide or RGD peptide mimetic.

Ligands can be proteins, e.g., glycoproteins, lipoproteins, e.g. low density lipoprotein (LDL), or albumins, e.g. human serum albumin (HSA), or peptides, e.g., molecules having a specific affinity for a co-ligand, or antibodies e.g., an antibody, that binds to a specified cell type such as a cancer cell, endothelial cell, or bone cell. Ligands may also include hormones and hormone receptors. They can also include non-peptidic species, such as cofactors, multivalent lactose, multivalent galactose, N-acetyl-galactosamine, N-acetyl-glucosamine, multivalent mannose, or multivalent fucose. The ligand can be, for example, a lipopolysaccharide, an activator of p38 MAP kinase, or an activator of NF-κB.

The ligand can be a substance, e.g, a drug, which can increase the uptake of the iRNA agent into the cell, for example, by disrupting the cell's cytoskeleton, e.g., by disrupting the cell's microtubules, microfilaments, and/or intermediate filaments. The drug can be, for example, taxon, vincristine, vinblastine, cytochalasin, nocodazole, japlakinolide, latrunculin A, phalloidin, swinholide A, indanocine, or myoservin.

In one aspect, the ligand is a lipid or lipid-based molecule. Such a lipid or lipid-based molecule binds a serum protein, e.g., human serum albumin (HSA). An HSA binding ligand allows for distribution of the conjugate to a target tissue, e.g., liver tissue, including parenchymal cells of the liver. Other molecules that can bind HSA can also be used as ligands. For example, neproxin or aspirin can be used. A lipid or lipid-based ligand can (a) increase resistance to degradation of the conjugate, (b) increase targeting or transport into a target cell or cell membrane, and/or (c) can be used to adjust binding to a serum protein, e.g., HSA.

A lipid based ligand can be used to modulate, e.g., control the binding of the conjugate to a target tissue. For example, a lipid or lipid-based ligand that binds to HSA more strongly will be less likely to be targeted to the kidney and therefore less likely to be cleared from the body. A lipid or lipid-based ligand that binds to HSA less strongly can be used to target the conjugate to the kidney. Also of interest are the lipid modifications described in WO/2005/023994; the disclosure of which is herein incorporated by reference.

In another aspect, the ligand is a moiety, e.g., a vitamin or nutrient, which is taken up by a target cell, e.g., a proliferating cell. These are particularly useful for treating disorders characterized by unwanted cell proliferation, e.g., of the malignant or non-malignant type, e.g., cancer cells. Exemplary vitamins include vitamin A, E, and K. Other exemplary vitamins include the B vitamins, e.g., folic acid, B12, riboflavin, biotin, pyridoxal or other vitamins or nutrients taken up by cancer cells.

In another aspect, the ligand is a cell-permeation agent, a helical cell-permeation agent. In some embodiments, the agent is amphipathic. An exemplary agent is a peptide such as tat or antennapedia. If the agent is a peptide, it can be modified, including a peptidylmimetic, invertomers, non-peptide or pseudo-peptide linkages, and use of D-amino acids. The helical agent may be an alpha-helical agent, which may have a lipophilic and a lipophobic phase.

In certain embodiments, iRNA agents are 5' phosphorylated or include a phosphoryl analog at the 5' prime terminus. 5'-phosphate modifications of the antisense strand include those which are compatible with RISC mediated gene silencing. Suitable modifications include: 5'-monophosphate ((HO)2(O)P—O-5'); 5'-diphosphate ((HO)2(O)P—O—P(HO)(O)—O-5'); 5'-triphosphate ((HO)2(O)P—O—(HO)(O)P—O—P(HO)(O)—O-5'); 5'-guanosine cap (7-methylated or non-methylated) (7m-G-O-5'-(HO)(O)P—O—(HO)(O)P—O—P(HO)(O)—O-5'); 5'-adenosine cap (Appp), and any modified or unmodified nucleotide cap structure. Other suitable 5'-phosphate modifications will be known to the skilled person.

The sense strand can be modified in order to inactivate the sense strand and prevent formation of an active RISC, thereby potentially reducing off-target effects. This can be accomplished by a modification which prevents 5'-phosphorylation of the sense strand, e.g., by modification with a 5'-O-methyl ribonucleotide (see Nykanen et al., (2001) ATP requirements and small interfering RNA structure in the RNA interference pathway. Cell 107, 309-321.) Other modifications which prevent phosphorylation can also be used, e.g., simply substituting the 5'-OH by H rather than O-Me. Alternatively, a large bulky group may be added to the 5'-phosphate turning it into a phosphodiester linkage.

Where desired, the nucleic acid, e.g., iRNA, DNA, etc, agents described herein can be formulated for administration to a subject, such as parenterally, e.g. via injection, orally, topically, to the eye, etc. As such, the nucleic acid can be combined with a pharmaceutically acceptable vehicle to provide a pharmaceutical composition. For ease of exposition, the formulations, compositions, and methods in this section are discussed largely with regard to unmodified iRNA agents. It should be understood, however, that these formulations, compositions, and methods can be practiced with other iRNA agents, e.g., modified iRNA agents, and such practice is within the invention.

A formulated iRNA agent composition can assume a variety of states. In some examples, the composition is at least partially crystalline, uniformly crystalline, and/or anhydrous (e.g., less than 80, 50, 30, 20, or 10% water). In another example, the iRNA agent is in an aqueous phase, e.g., in a solution that includes water, this form being the preferred form for administration via inhalation. The aqueous phase or the crystalline compositions can be incorporated into a delivery vehicle, e.g., a liposome (particularly for the aqueous phase), or a particle (e.g., a microparticle as can be appropriate for a crystalline composition). Generally, the iRNA agent composition is formulated in a manner that is compatible with the intended method of administration.

An iRNA agent preparation can be formulated in combination with another agent, e.g., another therapeutic agent or an agent that stabilizes an iRNA agent, e.g., a protein that complexes with the iRNA agent to form an iRNP. Still other agents include chelators, e.g., EDTA (e.g., to remove divalent cations such as Mg24), salts, RNAse inhibitors (e.g., a broad specificity RNAse inhibitor such as RNAsin) and so forth.

In one embodiment, the iRNA agent preparation includes another iRNA agent, e.g., a second iRNA agent that can mediate RNAi with respect to a second gene. Still other preparations can include at least three, five, ten, twenty, fifty, or a hundred or more different iRNA species. In some embodiments, the agents are directed to the same gene but different target sequences.

The nucleic acids can be formulated into pharmaceutical compositions by combination with appropriate, pharmaceutically acceptable vehicles, i.e., carriers or diluents, and may be formulated into preparations in solid, semi solid, liquid or gaseous forms, such as tablets, capsules, powders, granules, ointments, solutions, suppositories, injections, inhalants and aerosols. As such, administration of the agents can be achieved in various ways, including oral, buccal, rectal, parenteral, intraperitoneal, intradermal, transdermal, intracheal, etc., administration.

In pharmaceutical dosage forms, the agents may be administered alone or in appropriate association, as well as in combination, with other pharmaceutically active compounds. The following methods and excipients are merely exemplary and are in no way limiting.

For oral preparations, the agents can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The agents can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The agents can be utilized in aerosol formulation to be administered via inhalation. The compounds of the present invention can be formulated into pressurized acceptable propellants such as dichlorodifluoromethane, propane, nitrogen and the like.

Furthermore, the agents can be made into suppositories by mixing with a variety of bases such as emulsifying bases or water soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Nucleic acids may also be introduced into tissues or host cells by other routes, including microinjection, or fusion of vesicles. Jet injection may also be used for intramuscular administration, as described by Furth et al. (1992), Anal Biochem 205:365-368. The nucleic acids may be coated onto gold microparticles, and delivered intradermally by a particle bombardment device, or "gene gun" as described in the literature (see, for example, Tang et al. (1992), Nature 356:152 154), where gold microprojectiles are coated with the DNA, then bombarded into skin cells. Additional nucleic acid delivery protocols of interest include, but are not limited to: those described in U.S. patents of interest include U.S. Pat. No. 5,985,847 and U.S. Pat. No. 5,922,687 (the disclosures of which are herein incorporated by reference); WO/11092; Acsadi et al., New Biol. (1991) 3:71-81; Hickman et al., Hum. Gen. Ther. (1994) 5:1477-1483; and Wolff et al., Science (1990) 247: 1465-1468; etc. See e.g., the viral and non-viral mediated delivery protocols described above. Accordingly, of interest are pharmaceutical vehicles for use in such delivery methods.

The ribonucleic acids produced by embodiments of the methods find use in a variety of different applications, including but not limited to differential gene expression analysis, gene-silencing applications, nucleic acid library generation applications and therapeutic applications (e.g., in the production of antisense RNA, siRNA, etc.) Additional details regarding these types of utilities for RNA produced according to embodiments of the invention are provided in pending U.S. patent application Ser. No. 10/961,991 titled "Array-Based Methods for Producing Ribonucleic Acids," filed on Oct. 8, 2004 and published as US-2006-0078889-A1 on Apr. 13, 2006; the disclosure of which is herein incorporated by reference.

Kits

Also of interest are kits for use in practicing certain embodiments of the invention. In certain embodiments, kits include at least 2 different protected monomers, e.g., 2' orthoester-type protected nucleoside monomers which include a second, aryl carbonate-type, protecting group in accordance with the invention, where the kits may include the monomers that have the same nucleobase or monomers that include different nucleobases, e.g., A, G, C and U. The kits may further include additional reagents employed in methods of the invention, e.g., buffers, oxidizing agents, capping agents, cleavage agents, etc. In certain embodiments, the kits will further include instructions for practicing the subject methods or means for obtaining the same (e.g., a website URL directing the user to a webpage which provides the instructions), where these instructions may be printed on a substrate, where substrate may be one or more of: a package insert, the packaging, reagent containers and the like. In the subject kits, the one or more components are present in the same or different containers, as may be convenient or desirable.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A ribonucleoside monomer having the structure:

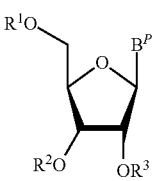

I wherein $B^P$ is uracil or an amino-protected heterocyclic base, wherein said amino-protected heterocyclic base is selected to be unreactive during steps of ribonucleoside monomer synthesis and polynucleotide synthesis; and one of $R^1$ or $R^2$ is an aryl carbonate-type hydroxyl protecting group having the structure:

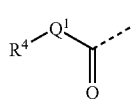

II wherein the dashed line indicates the site at which said aryl carbonate-type protecting group is bound to the 3' or 5' oxygen of said ribonucleoside monomer;

$Q^1$ is an oxygen or a sulfur atom; and $R^4$ is an aryl group or a substituted aryl group;

the other of $R^1$ or $R^2$ is selected from hydrogen, a protecting group, and a phosphoramidite group; and $R^3$ is an orthoester-type 2' hydroxyl protecting group having the structure:

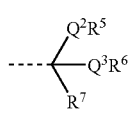

V wherein the dashed line indicates the site at which $R^3$ is bound to the 2' oxygen of said ribonucleoside monomer;

$Q^2$ and $Q^3$ are each independently either a sulfur or an oxygen atom;

$R^5$ and $R^6$ are each independently selected from a hydrocarbyl, a substituted hydrocarbyl, an aryl, a substituted aryl, or $R^5$ and $R^6$, together with $Q^2$, $Q^3$ and the carbon to which $Q^2$ and $Q^3$ are attached are cyclically linked to form a heterocyclic group; and $R^7$ is selected from hydrogen, a hydrocarbyl, a substituted hydrocarbyl, an aryl, and a substituted aryl.

2. The ribonucleoside monomer according to claim 1, wherein $Q^2$ and $Q^3$ are each a sulfur atom.

3. The ribonucleoside monomer according to claim 1, wherein $Q^1$ is an oxygen atom.

4. The ribonucleoside monomer according to claim 1, wherein $R^4$ is a phenyl group or a substituted phenyl group.

5. The ribonucleoside monomer according to claim 4, wherein $R^4$ has the structure:

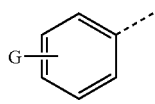

III wherein:
the dashed line indicates the site at which $R^4$ is bound to $Q^1$; and G is one or more substituent groups each independently selected from a lower hydrocarbyl, a substituted lower hydrocarbyl, an aryl, a substituted aryl, a halogen, a cyano, an amino, a nitro, a sulfate, an alkyl thiolate, a substituted alkyl thiolate, a nitrate, and a carbonate.

6. The ribonucleoside monomer according to claim 5, wherein $R^4$ has the structure:

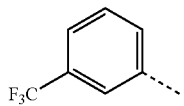

IV wherein the dashed line indicates the site at which $R^4$ is bound to $Q^1$.

7. The ribonucleoside monomer according to claim 1, wherein $R^5$ and $R^6$, together with $Q^2$, $Q^3$ and the carbon to which $Q^2$ and $Q^3$ are attached are cyclically linked to form a heterocyclic group.

8. The ribonucleoside monomer according to claim 7, wherein $R^3$ has the structure:

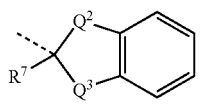

VI wherein the dashed line indicates the site at which $R^3$ is bound to the 2' oxygen of said ribonucleoside monomer.

9. The ribonucleoside monomer according to claim 8, wherein $R^3$ has the structure:

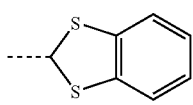

VII wherein the dashed line indicates the site at which $R^3$ is bound to the 2' oxygen of said ribonucleoside monomer.

10. A method of coupling a ribonucleoside monomer to a nucleoside residue comprising:
(a) providing a nucleoside residue having an unprotected hydroxyl group and the ribonucleoside monomer of claim 1, wherein:
one of $R^1$ or $R^2$ is a phosphoramidite group; and
the other of $R^1$ or $R^2$ is an aryl carbonate-type hydroxyl protecting group; and
(b) contacting said nucleoside residue with said ribonucleoside monomer under conditions sufficient to covalently bond said ribonucleoside monomer to said nucleoside residue via a phosphite triester linkage to produce said coupled nucleoside residue-ribonucleoside monomer.

11. The method according to claim 10, wherein said method further comprises:
contacting said coupled nucleoside residue-ribonucleoside monomer with a peroxide, thereby oxidizing said phosphite triester linkage and deprotecting said aryl carbonate-type hydroxyl protecting group to produce a polynucleotide intermediate.

12. The method according to claim 11, wherein said method further comprises reiterating said providing step and said contacting steps until a desired polynucleotide sequence is obtained.

13. The method according to claim 12, wherein said method further comprises removing said orthoester-type 2' hydroxyl protecting group of said polynucleotide by contacting said polynucleotide with an acid.

14. The method according to claim 12, wherein said nucleoside residue is covalently bound to a solid support.

15. The method according to claim 14, wherein said method further comprises cleaving said polynucleotide from said solid support to produce a free polynucleotide.

16. The method according to claim 15, wherein said method further comprises chemically modifying said free polynucleotide to produce a modified polynucleotide.

17. The method according to claim 16, wherein said method further comprises combining said modified polynucleotide with a pharmaceutically acceptable vehicle.

18. The method according to claim 15, wherein said method further comprises combining said free polynucleotide with a pharmaceutically acceptable vehicle.

19. The method according to claim 14, wherein said method further comprises chemically modifying said polynucleotide to produce a modified polynucleotide, and then cleaving said modified polynucleotide from said solid support.

20. A polynucleotide having the structure of Formula (I):

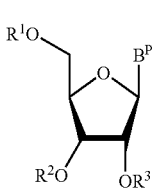

I wherein $B^P$ is uracil or an amino-protected heterocyclic base, wherein said amino-protected heterocyclic base is selected to be unreactive during steps of synthesis of said polynucleotide;

one of $R^1$ or $R^2$ is an aryl carbonate-type hydroxyl protecting group having the structure:

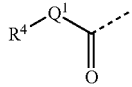     II wherein the dashed line indicates the site at which said aryl carbonate-type hydroxyl protecting group is bound to the 3' or 5' oxygen of the structure of Formula (I);
$Q^1$ is an oxygen or a sulfur atom; and
$R^4$ is an aryl group or a substituted aryl group;
the other of $R^1$ or $R^2$ has the structure:

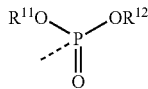     XI wherein the dashed line indicates the site at which said other of $R^1$ or $R^2$ is bound to the 3' or 5' oxygen of the structure of Formula (I);

$R^{11}$ is selected from the group consisting of hydrogen, a hydrocarbyl, a substituted hydrocarbyl, an aryl, and a substituted aryl; and
$R^{12}$ is a nucleoside residue; and
$R^3$ is an orthoester-type 2' hydroxyl protecting group having the structure:

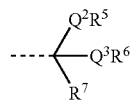     V wherein the dashed line indicates the site at which $R^3$ is bound to the 2' oxygen of the structure of Formula (I);
$Q^2$ and $Q^3$ are each independently either a sulfur or an oxygen atom;
$R^5$ and $R^6$ are each independently selected from a hydrocarbyl, a substituted hydrocarbyl, an aryl, a substituted aryl, or $R^5$ and $R^6$, together with $Q^2$, $Q^3$ and the carbon to which $Q^2$ and $Q^3$ are attached are cyclically linked to form a heterocyclic group; and
$R^7$ is selected from hydrogen, a hydrocarbyl, a substituted hydrocarbyl, an aryl, and a substituted aryl.

* * * * *

UNITED STATES PATENT AND TRADEMARK OFFICE
CERTIFICATE OF CORRECTION

PATENT NO. : 8,242,258 B2 Page 1 of 1
APPLICATION NO. : 11/949667
DATED : August 14, 2012
INVENTOR(S) : Douglas J. Dellinger et al.

It is certified that error appears in the above-identified patent and that said Letters Patent is hereby corrected as shown below:

Title Page, Item (56), under "U.S. Patent Documents", in column 1, line 9, delete "Dollinger et al." and insert -- Dellinger et al. --, therefor.

Signed and Sealed this
Second Day of October, 2012

David J. Kappos
*Director of the United States Patent and Trademark Office*